United States Patent
Xiao et al.

(10) Patent No.: US 11,656,235 B2
(45) Date of Patent: May 23, 2023

(54) DNA APTAMER-CYANINE COMPLEXES AS MEPHEDRONE AND CANNABINOID COLORIMETRIC SENSORS

(71) Applicants: Yi Xiao, Miami, FL (US); Obtin Alkhamis, Miami, FL (US); Haixiang Yu, Miami, FL (US)

(72) Inventors: Yi Xiao, Miami, FL (US); Obtin Alkhamis, Miami, FL (US); Haixiang Yu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/396,663

(22) Filed: Aug. 7, 2021

(65) Prior Publication Data

US 2023/0054132 A1     Feb. 23, 2023

(51) Int. Cl.
   *G01N 33/94*        (2006.01)
   *G01N 21/78*        (2006.01)
   *G01N 33/58*        (2006.01)

(52) U.S. Cl.
   CPC ......... *G01N 33/9486* (2013.01); *G01N 21/78* (2013.01); *G01N 33/583* (2013.01); *G01N 33/946* (2013.01); *G01N 33/948* (2013.01); *G01N 33/9413* (2013.01)

(58) Field of Classification Search
   CPC .. G01N 33/9486; G01N 21/78; G01N 33/583; G01N 33/9413; G01N 33/946; G01N 33/948
   USPC ............................................. 436/91–98, 166
   See application file for complete search history.

(56) References Cited

U.S. PATENT DOCUMENTS

| | | | | |
|---|---|---|---|---|
| 5,658,751 A | * | 8/1997 | Yue | C07D 215/18 435/29 |
| 7,381,531 B2 | * | 6/2008 | Stojanovic | G01N 33/566 435/6.11 |
| 7,470,516 B2 | * | 12/2008 | Stojanovic | C07H 21/02 435/6.11 |
| 8,084,204 B2 | * | 12/2011 | Stojanovic | G01N 33/566 435/6.1 |
| 9,804,178 B2 | * | 10/2017 | Roncancio | C12N 15/115 |

(Continued)

OTHER PUBLICATIONS

Stojanovic, M. N. et al, Journal of the American Chemical Society 2002, 124, 9678-9679.*

(Continued)

*Primary Examiner* — Arlen Soderquist
(74) *Attorney, Agent, or Firm* — Saliwanchik, Lloyd & Eisenschenk

(57) ABSTRACT

The subject invention provides materials and methods for single-step detection of target molecules in a sample. The methods and assays of the subject invention employ a dye-displacement strategy, in which aptamers complexed with a cyanine dye for sensitive and rapid detection of targets of interest. In the presence of a target, aptamer-target binding liberates the non-covalently bound aptamer-binding dye, resulting in optical changes that can be observed spectrophotometrically or with the naked eye. The methods and assays of the subject invention enable the colorimetric detection of targets of interest regardless of their structure, sequence, target-binding affinity, and physicochemical properties of their targets.

20 Claims, 17 Drawing Sheets

Specification includes a Sequence Listing.

DNA Aptamers

Dye-aptamer complex

(56) References Cited

U.S. PATENT DOCUMENTS

| | | | |
|---|---|---|---|
| 10,550,395 B2* | 2/2020 | Xiao | G01N 33/946 |
| 10,655,132 B1* | 5/2020 | Yang | A61K 31/167 |
| 10,683,507 B2* | 6/2020 | Xiao | G01N 33/50 |
| 10,907,162 B2* | 2/2021 | Yang | G01N 27/3276 |
| 10,907,163 B1* | 2/2021 | Xiao | G01N 33/948 |
| 11,060,095 B2* | 7/2021 | Yang | G01N 27/3276 |
| 11,408,850 B2* | 8/2022 | Xiao | G01N 27/3276 |
| 2003/0198966 A1* | 10/2003 | Stojanovic | G01N 33/566 435/6.13 |
| 2005/0130208 A1* | 6/2005 | Stojanovic | G01N 33/566 435/6.13 |
| 2005/0191620 A1* | 9/2005 | McDevitt | G01N 21/6452 435/5 |
| 2005/0202503 A1* | 9/2005 | Stojanovic | G01N 33/566 435/6.11 |
| 2006/0172320 A1* | 8/2006 | Stojanovic | C12N 15/115 435/6.12 |
| 2006/0257941 A1* | 11/2006 | McDevitt | G01N 1/4077 435/7.2 |
| 2006/0257992 A1* | 11/2006 | McDevitt | B01L 3/502715 435/287.2 |
| 2008/0286877 A1* | 11/2008 | Stojanovic | G01N 33/566 436/86 |
| 2010/0197516 A1* | 8/2010 | Holmes | G01N 31/22 506/9 |
| 2016/0131668 A1* | 5/2016 | Roncancio | G01N 33/946 436/501 |
| 2019/0256852 A1* | 8/2019 | Xiao | C07C 225/10 |
| 2019/0309296 A1* | 10/2019 | Xiao | G01N 33/92 |
| 2020/0131514 A1* | 4/2020 | Yang | G01N 27/26 |
| 2020/0172907 A1* | 6/2020 | Yang | G01N 27/3276 |
| 2021/0102210 A1* | 4/2021 | Yang | A61K 31/167 |
| 2021/0396706 A1* | 12/2021 | Xiao | G01N 27/3276 |

OTHER PUBLICATIONS

Liu, Y. et al, Analytical Chemistry 2005, 77, 2450-2454.*
Zhou, C. et al, Analytical and Bioanalytical Chemistry 2006, 384, 1175-1180.*
Nguyen, B. T. et al, Coordination Chemistry Reviews 2006, 250, 3118-3127.*
Monchaud, D. et al, Bioorganic & Medicinal Chemistry Letters 2006, 16, 4842-4845.*
Monchaud, D. et al, Biochimie 2008, 90, 207-1223.*
Paramasivan, S. et al, Nucleic Acids Research, 2008, 36, paper e106, 9 pages with 8 pages of supplementary material.*
Liu, J. et al, Chemical Reviews 2009, 109, 1948-1998.*
He, J.-L. et al, Analytical Chemistry 2010, 82, 1358-1364.*
Strehlitz, B. et al, Bioanalytical Reviews 2012, 4, 1-30.*
Ren, J. et al, Biosensors and Bioelectronics 2012, 35, 401-406.*
Sun, H. et al, Analyst 2012, 137, 5713-5715.*
Vummidi, B. R. et al, ChemBioChem 2013, 14, 540-558.*
Kretschy, N. et al, PLOS One 2014, 9, Paper e85605, 5 pages.*
Roncancio, D. et al, Analytical Chemistry 2014, 86, 11100-11106.*
Guo, Y. et al, Microchimica Acta 2016, 183, 21-34.*
Wang, J. et al, Taianta 2016, 161, 437-442.*
Chovelon, B. et al, Biosensors and Bioelectronics 2017, 90, 140-145.*
Pode, Z. et al, Nature Nanotechnology 2017, 12, 1161-68 with 52 pages of supplementary information.*
Musumeci, D. et al, Cancers 2017, 9, paper 174, 43 pages.*
Sun, C. et al, Dyes and Pigments 2018, 149, 867-875.*
Bouhedda, F. et al, International Journal of Molecular Sciences 2018, 19, paper 44, 21 pages.*
Yu, H. et al, Nucleic Acids Research 2018, 46, paper e43, 9 pages with 8 pages of supplementary data.*
Garrido, E. et al, ChemistryOpen 2018, 7, 401-428.*
Canoura, J. et al, Journal of the American Chemical Society 2018, 140, 9961-9971 with 12 pages of supporting information.*
Nakatsuka, N. et al, Science2018, 362, 319-324 with 44 pages of supplementary materials.*
Li, Y. et al, Microchimica Acta 2019, 186, paper 214, 7 pages.*
Yang, W. et al, Nucleic Acids Research 2019, 47, paper e71, 10 pages with 17 pages of supplementary data.*
Wicks, S. L. et al, Methods 2019, 167, 3-14.*
Xu, G. et al, Nucleic Acids Research 2019, 47, 5963-5972.*
Kammer, M. N. et al, Analytical Chemistry 2019, 91, 10582-10588 with 11 pages of supporting information.*
Deore,, P. S. et al, Journal of the American Chemical Society 2019, 141, 14288-14297 with 9 pages of supporting information.*
Alkhamis, O. et al, Trends in Analytical Chemistry 2019, 121, paper 115699, 11 pages.*
Zhou, Y. et al, Current Opinion in Biomedical Engineering 2020, 13, 16-24.*
Liu, Y. et al, Analytical Chemistry 2020, 92, 5041-5047 with 30 pages of supporting information.*
Alkhamis, O. et al., Nucleic Acids Research 2020, 48, paper e120, 11 pages with 34 pages of supplementary information.*
Canoura, J. et al, Journal of the American Chemical Society 2021, 143, 805-816 with 31 pages of supporting information.*
Yu, H. et al, Analytical Chemistry 2021, 93, 3172-3180 with 24 pages of supporting information.*
Nakatsuka, N. et al, Analytical Chemistry 2021, 93, 4033-4041.*
Buschmann, V. et al,Bioconjugate Chemistry 2003, 14, 195-204.*
Sayama, K. et al, Solar Energy Materials & Solar Cells 2003, 80, 47-71.*
Sovenyhazy, K. M. et al, Nucleic Acids Research 2003, 31, 2561-2569.*
Yang, Q. et al, Nucleic Acids Research, 2010, vol. 38, 1022-1033 with 11 pages of supporting information.*
Nicoli, F. et al, Journal of Physical Chemistry A 2016, 120, 9941-9947 with 7 pages of supporting information.*
Harbater, O. et al, Applied Sciences 2018, 8, paper 745, 14 pages.*
Berlepsch, H. V. et al, Phys. Chem. Chem. Phys., 2018, 20, 18969-18977 with 5 pasges of supplementary information.*
Kay, R. E. et al, Journal of Physical Chemistry 1964, 68, 1896-1906.*
Lu, M. et al, Biochemistry 1990, 29, 3407-3412.*
Banerjee, D. et al, Journal of Photochemistry and Photobiology A: Chemistry 1996, 98, 183-186.*
Gruber, H. J. et al, Bioconjugate Chemistry 2000, 11, 696-704.*
Peyratout, C et al, Journal of Photochemistry and Photobiology A: Chemistry 2001, 142, 51-57.*
Kang, J. et al, International Journal of Polymer Science 2010, Article ID 264781, 7 pages.*
Yang, Q. et al, Analytical Chemistry 2010, 82, 9135-9137 and 19 pages of supplementary information.*
Choi, J. K. et al, International Journal of Molecular Sciences 2011, 12, 8052-8062.*
Sun, H. et al, Chemical Commununications 2013, 49, 4510-4512 and 12 pages of supplementary material.*
Chen, H. et al, Analyst 2015, 140, 7170-7174 and 4 pages of supplementary material.*
Zhang, S. et al, Analytical Methods 2016, 8, 3740-3746.*
Yang, D et al, Analytical Methods 2019, 11, 4249-4253 and 4 pages of supplementary material.*

* cited by examiner

FIG. 1A
FIG. 1B
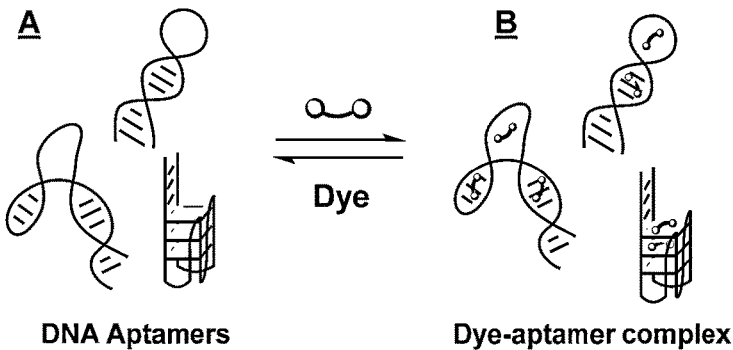
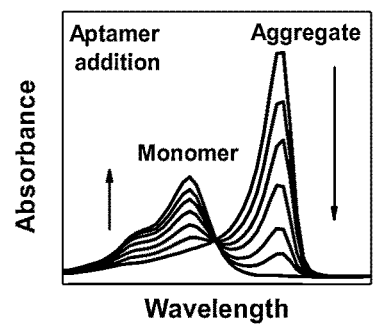
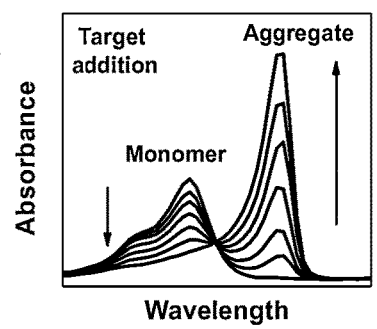
FIG. 1C
FIG. 1D
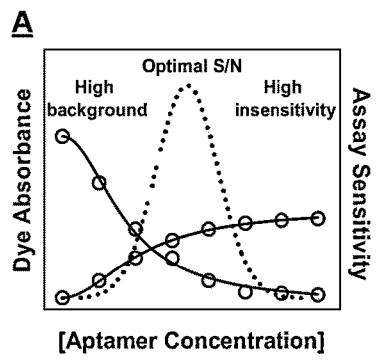
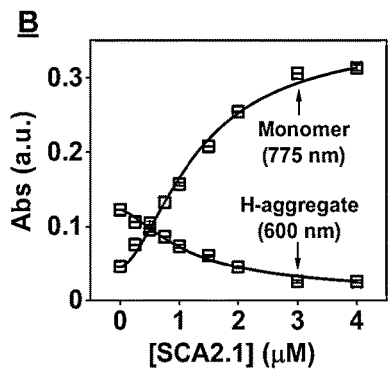
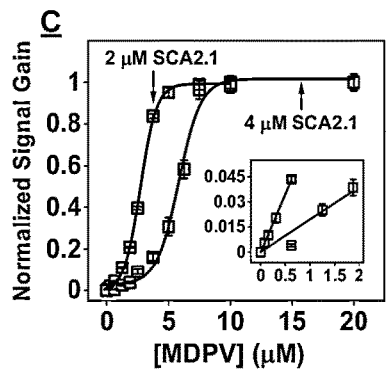
FIG. 2A
FIG. 2B
FIG. 2C

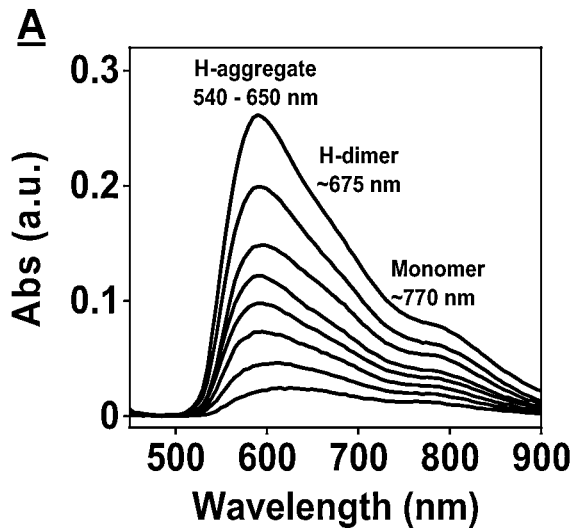 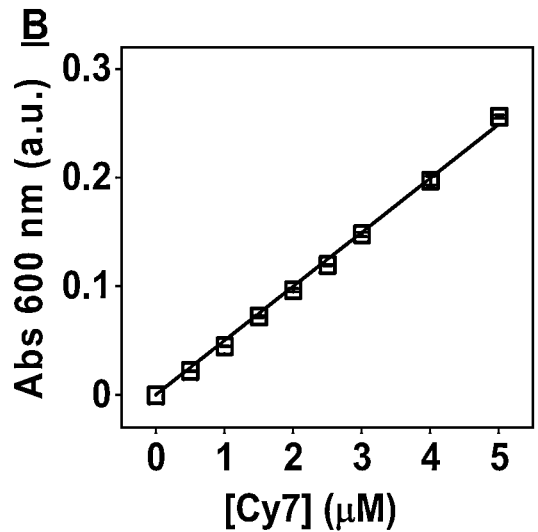
FIG. 3A
FIG. 3B
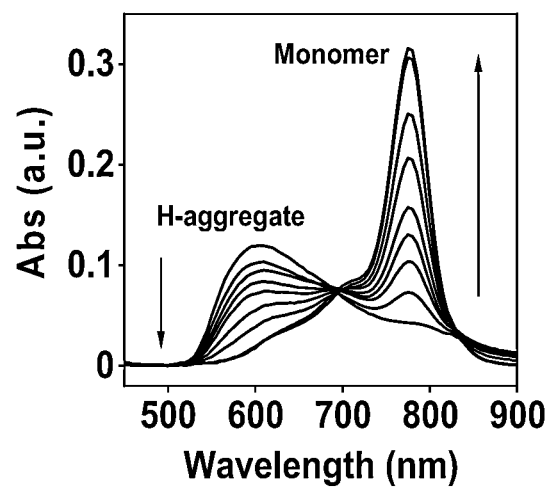
FIG. 4

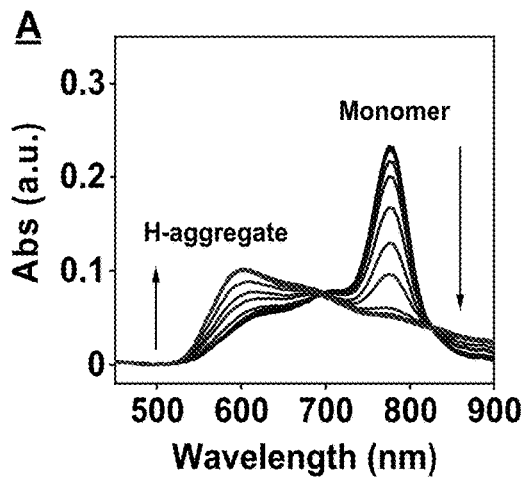
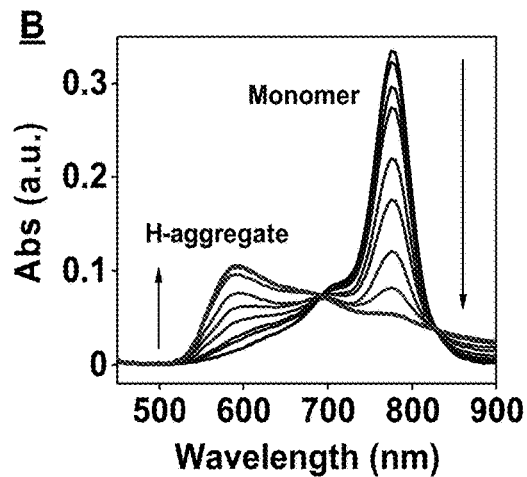
FIG. 5A    FIG. 5B
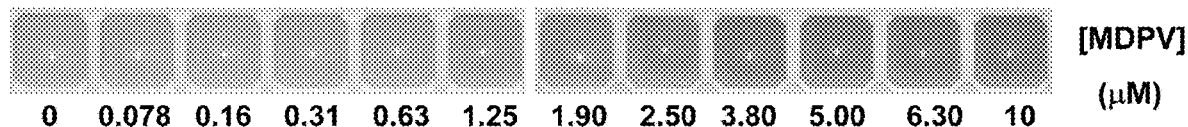
FIG. 6

FIG. 7A
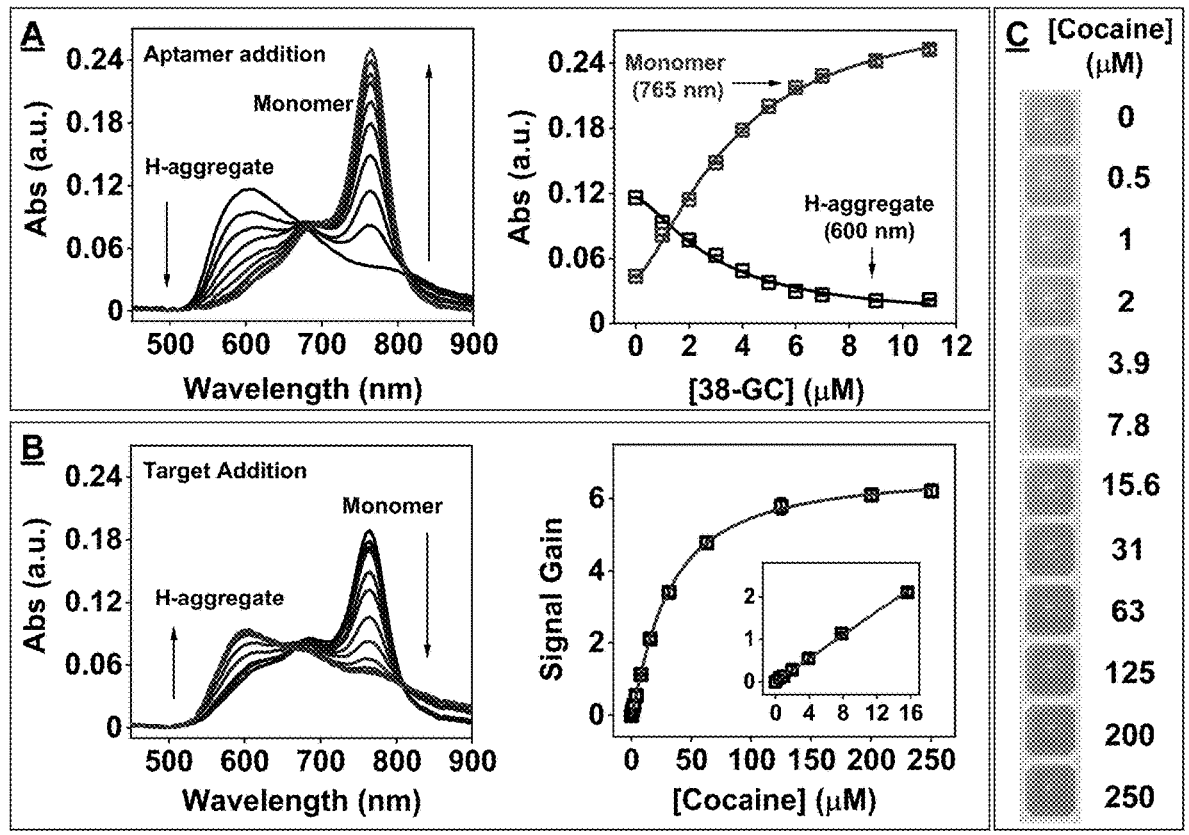
FIG. 7B  FIG. 7C
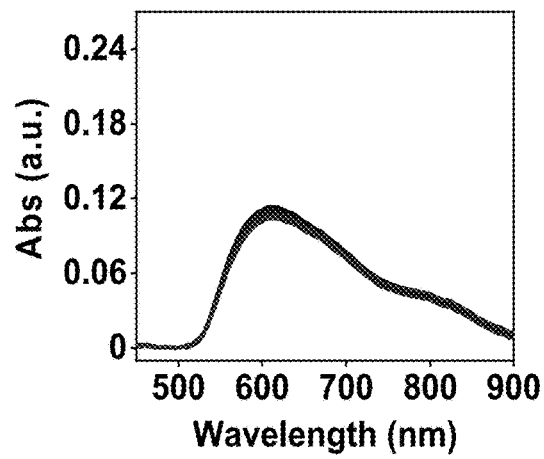
FIG. 8

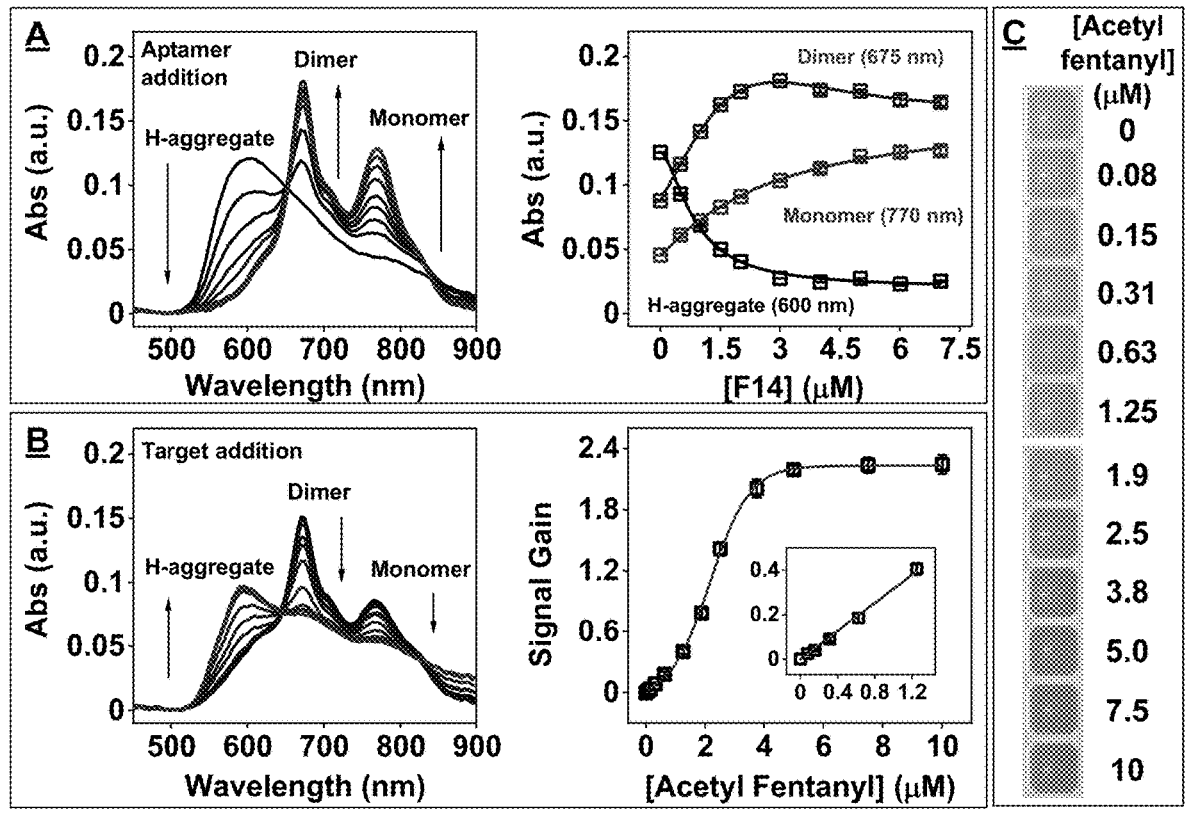
FIG. 9A
FIG. 9B  FIG. 9C
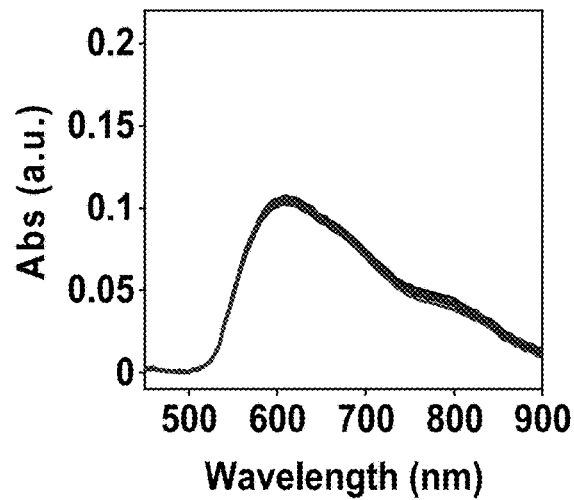
FIG. 10

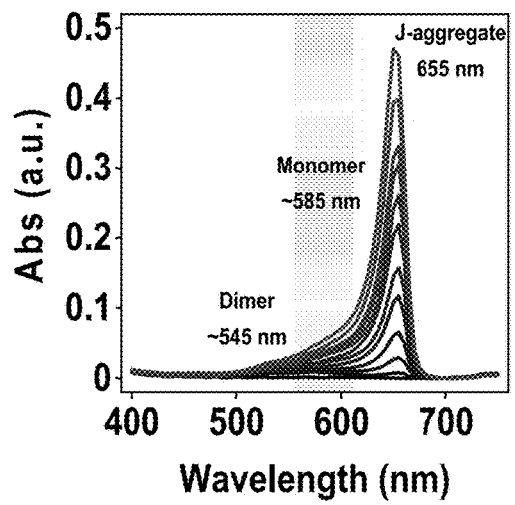
FIG. 11
FIG. 12A       FIG. 12B       FIG. 12C
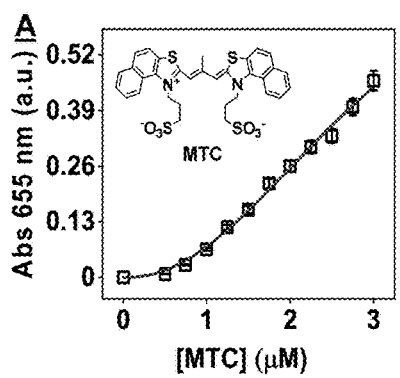 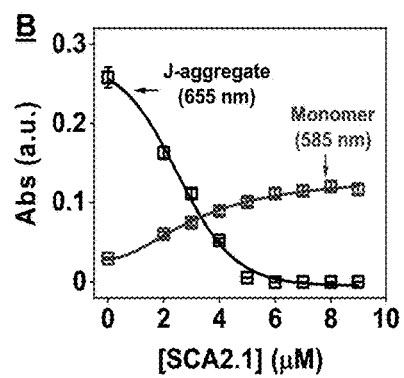 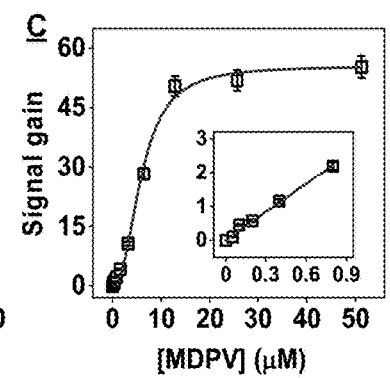
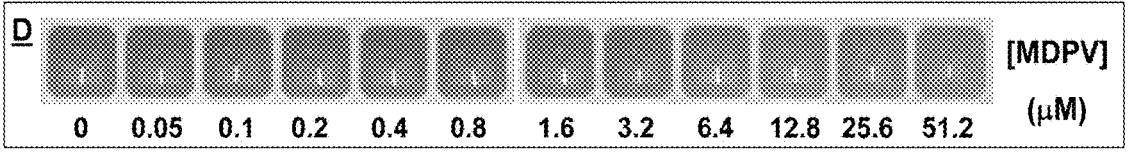
FIG. 12D

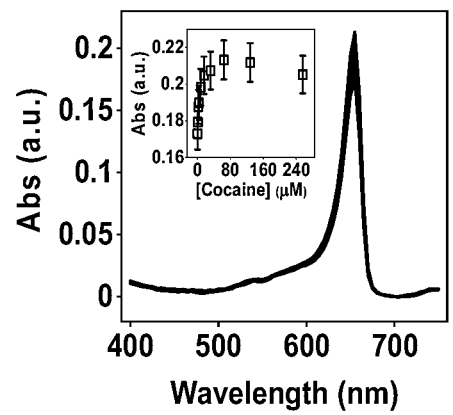
FIG. 18
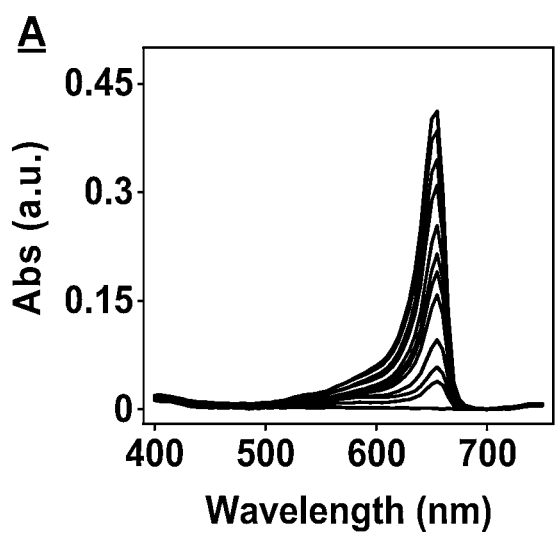 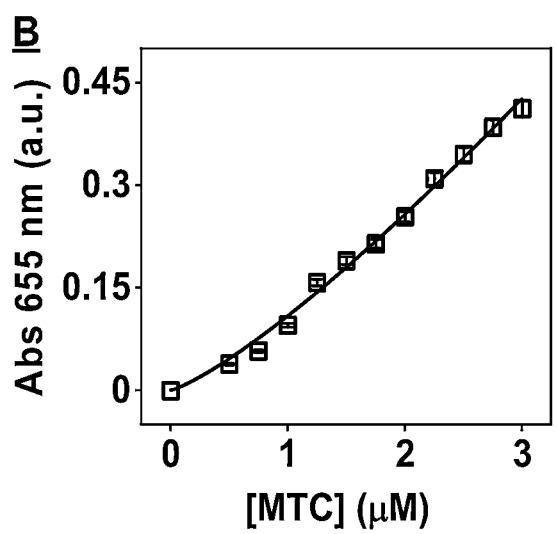
FIG.19A    FIG. 19B

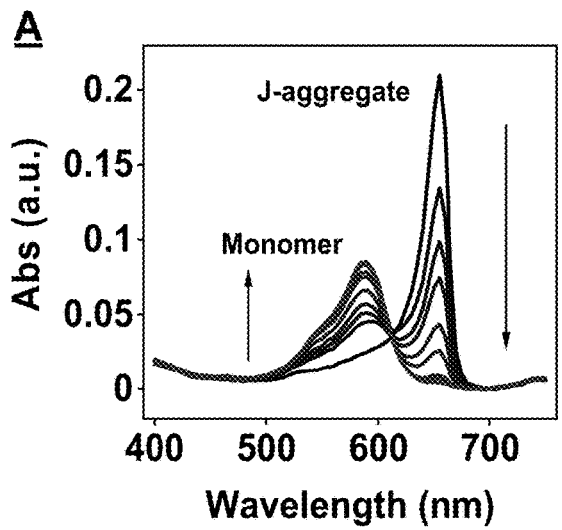
FIG. 20A
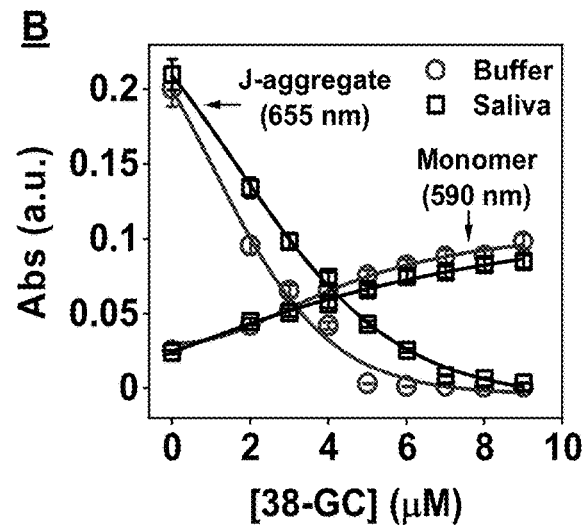
FIG. 20B
FIG. 21A
FIG. 21B
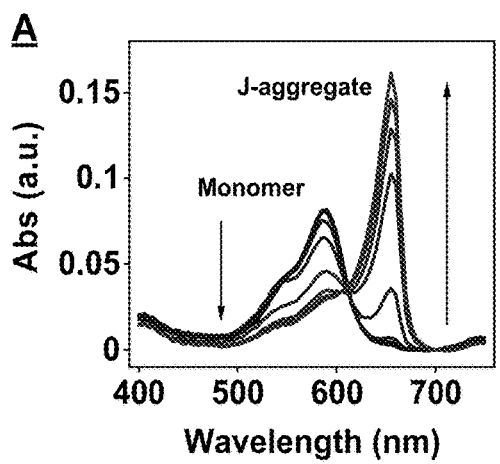
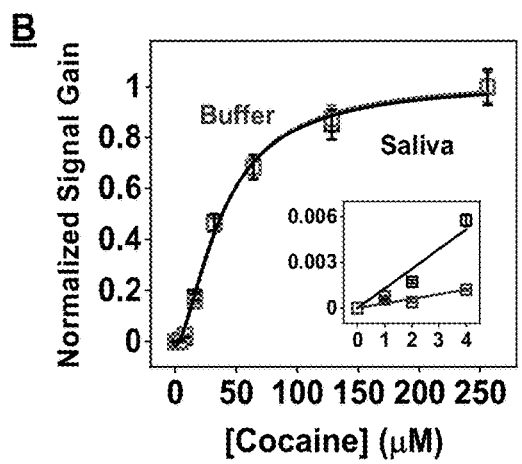
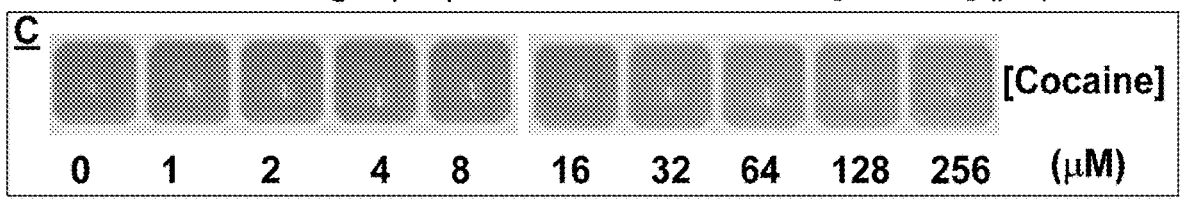
FIG. 21C

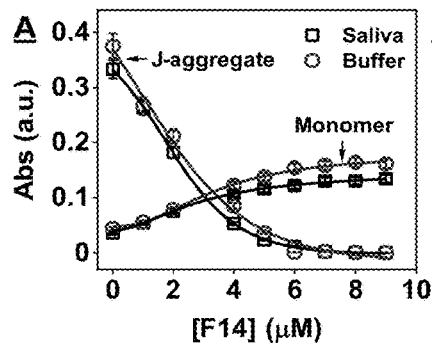 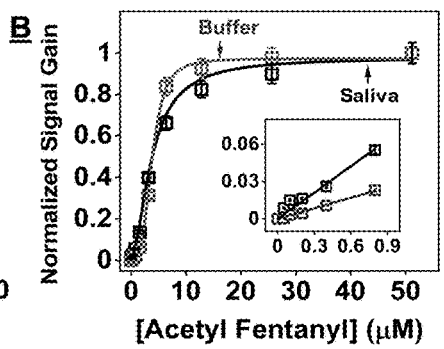 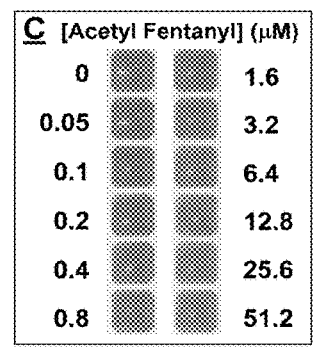
FIG. 22A  FIG. 22B  FIG. 22C
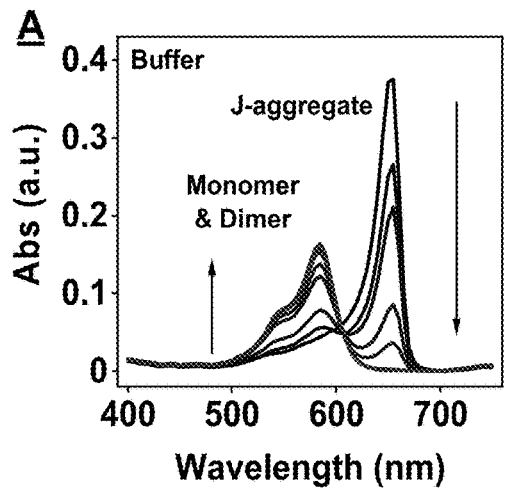 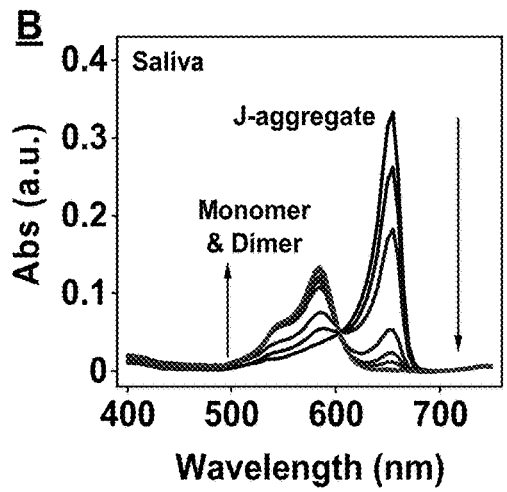
FIG. 23A  FIG. 23B
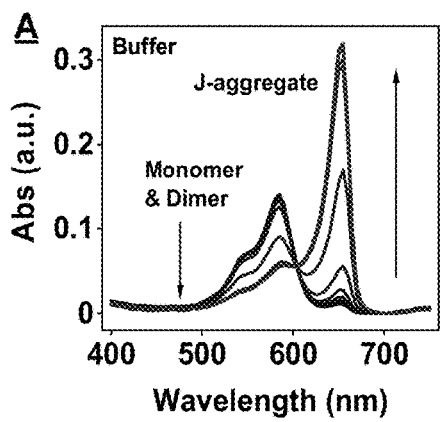 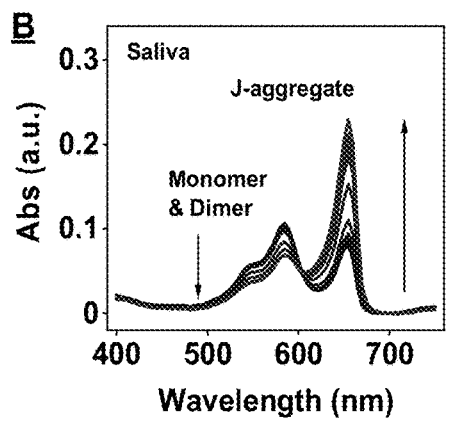
FIG. 24A  FIG. 24B

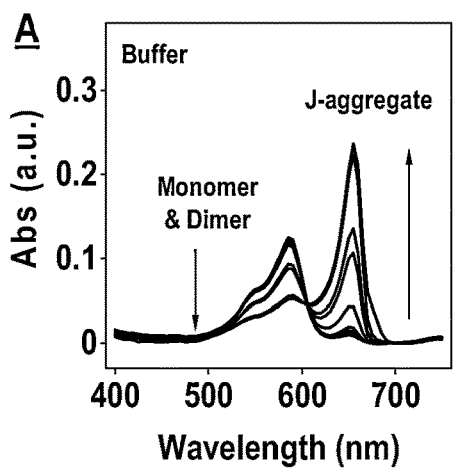
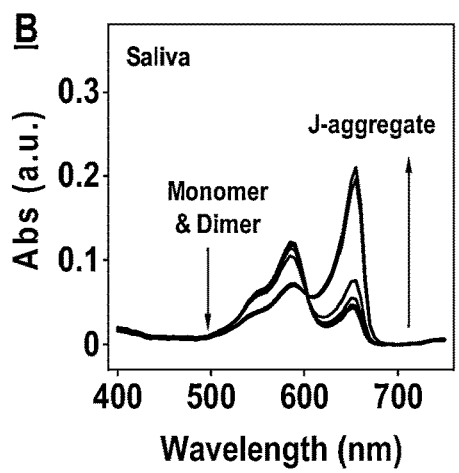
FIG. 29A   FIG. 29B
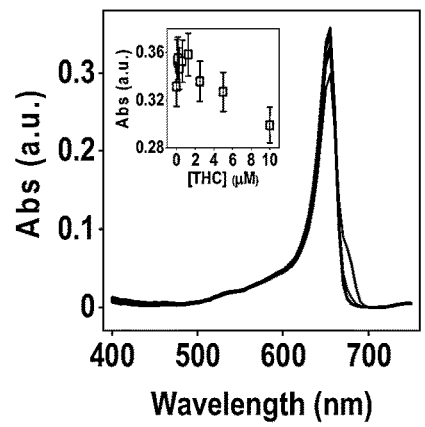
FIG. 30
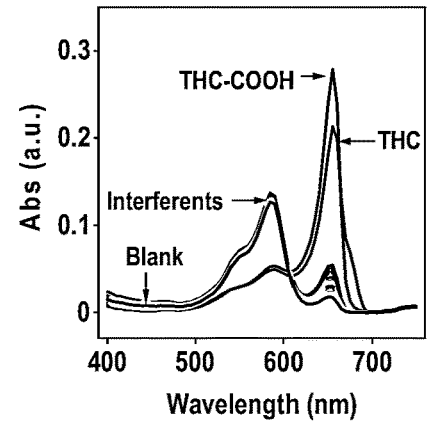
FIG. 31

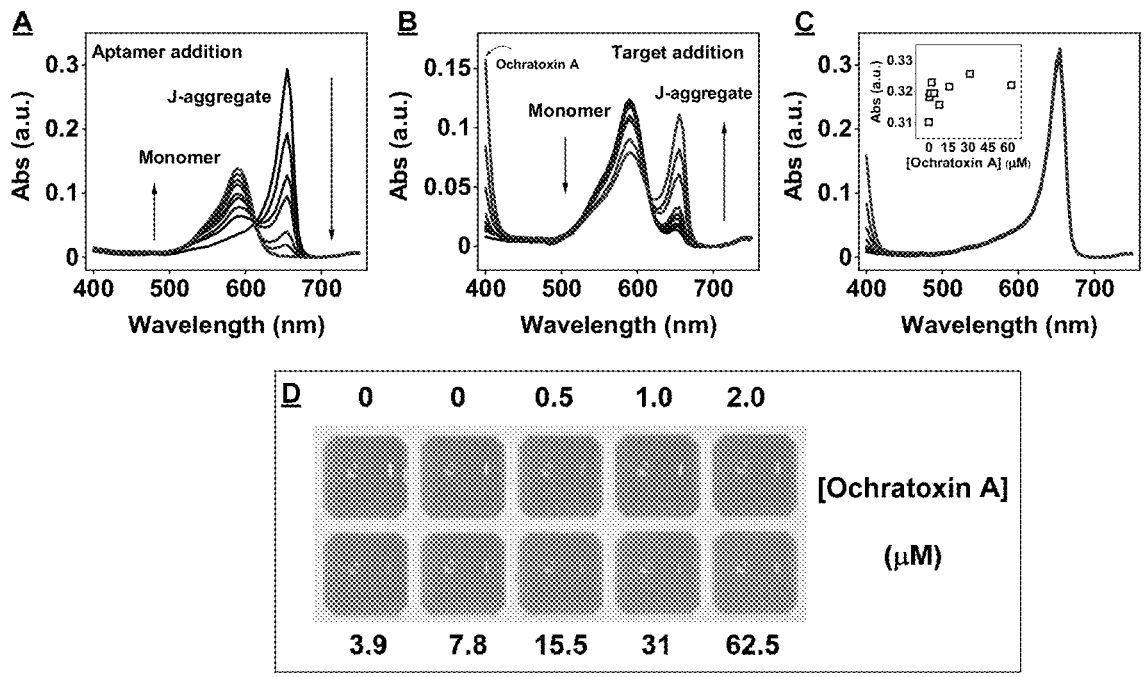
FIG. 33A  FIG. 33B  FIG. 33C
FIG. 33D
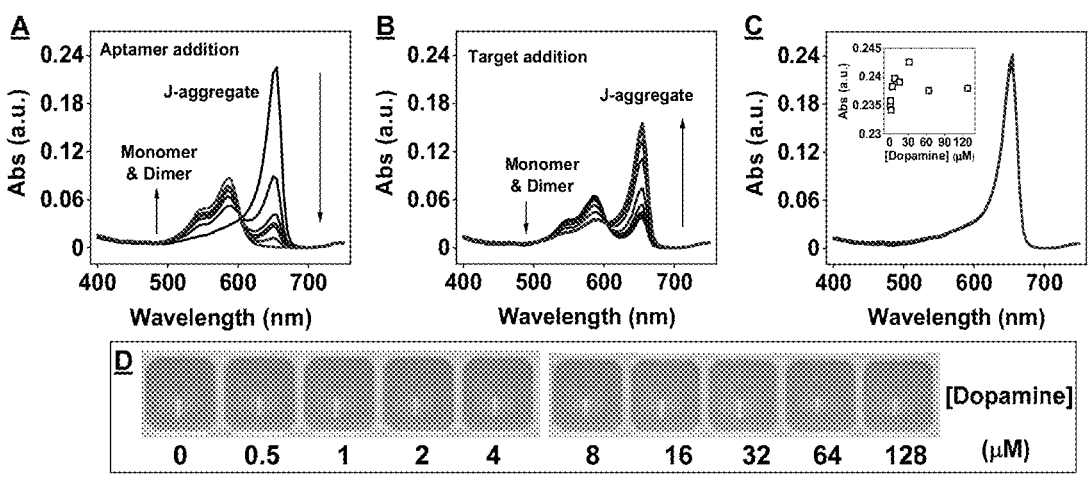
FIG. 34A  FIG. 34B  FIG. 34C
FIG. 34D

DNA APTAMER-CYANINE COMPLEXES AS MEPHEDRONE AND CANNABINOID COLORIMETRIC SENSORS

GOVERNMENT SUPPORT

This invention was made with government support under Grant No. CHE1905143 awarded by the National Science Foundation. The government has certain rights in the invention.

SEQUENCE LISTING

The Sequence Listing for this application is labeled "SeqList-22Jun21-ST25.txt," which was created on Jun. 22, 2021, and is 2 KB. The Sequence Listing is incorporated herein by reference in its entirety.

BACKGROUND OF THE INVENTION

Aptamers are short oligonucleotides that are typically isolated from randomized libraries through in vitro methods. Aptamers bind to substances such as ions, small molecules, and proteins with high affinity and specificity. They have attracted widespread attention for the development of accurate and affordable sensors that can be used on-site or at the point-of-care.

Aptamers are ideal biorecognition elements because they can be rapidly generated and synthesized at a low cost with minimal batch-to-batch variability, have long shelf lives, and can be employed in a variety of sensing platforms and in physicochemical conditions inimical to antibodies, such as high temperatures and a broad range of pH levels and ionic strengths. Owing to their unique advantages, aptamers have permitted scientific breakthroughs previously inaccessible by antibody technologies, such as both the real-time monitoring of molecular trafficking within cells and in live organisms in vivo.

Despite the great promise of aptamers for biosensing, many aptamer-based assays reported to date are incapable of being used in practical contexts due to their poor sensitivity and selectivity. These inadequacies stem from two sources. First, many assays rely on aptamers to undergo a major conformational change upon target binding to produce detectable signals. Nearly universally, aptamers with conformation changing capabilities, such as structure-switching aptamers, split aptamers, or aptamers hybridized with complementary DNA probes, have at least 10-fold greater dissociation constants ($K_D$) relative to their parental aptamers, and expectedly, the analytical performance of sensors made using these aptamers often fail to meet the level necessary for practical use. Second, the need for aptamer labeling with signal reporters such as fluorophores, gold nanoparticles, or quantum dots increases assay cost and complexity, while assays that utilize certain non-covalent reporters such as gold nanoparticles have unacceptably high rates of false results due to non-specific triggering of signals by factors unrelated to the target analyte.

Alternatively, dye-displacement assays are a lucrative sensing modality based on organic small molecule dyes and native non-engineered aptamers. They are a highly attractive means of analyte detection due to their simplicity of development and execution, high sensitivity, low cost, and rapidity. A dye molecule is initially complexed with an aptamer, and target binding to the aptamer causes the dye to become released into solution either through direct displacement by the target or the induction of a subtle conformational change in the aptamer. Signals are produced based on the principle that the aptamer-bound and solution-free forms of the dye have differing optical properties, and thus the target can be detected by measuring changes in dye absorbance or fluorescence. The utilization of dye-displacement assays has been limited by the unknown compatibility of aptamer sequence and structure, target analyte identity and properties, and sensing condition requirements for proper assay function and the lack of a general strategy to develop sufficiently responsive assays.

Importantly, because the signal transduction event does not require the aptamer to undergo major conformational changes, the need for aptamer engineering is eliminated, and therefore these assays can be label-free and highly sensitive due to the employment of parental aptamers, which have much greater affinity than their conformation changing counterparts. Nevertheless, the utilization of these assays has been limited by their seemingly limited general applicability among aptamers with varying sequences and structures. For instance, several works have demonstrated that nucleic acid binding dyes such as SYBR Green I, TOTO, and certain organometallic complexes can be employed with select DNA and RNA aptamers for the detection of small molecules and proteins. However, as these studies have not explored assay generality beyond one or a few combinations of dyes, aptamers, and targets, definitive factors that are essential for successful assay operation have yet to be identified.

Thus, there is a need to develop methods and assays that enable the detection of a target of interest using, for example, the cyanine dye in the displacement assay regardless of the aptamer structure, sequence, target-binding affinity, or physicochemical properties of their targets.

BRIEF SUMMARY OF THE INVENTION

The subject invention provides materials and methods that enable the utilization of aptamers in dye-displacement assay format with cyanine dyes regardless of aptamer sequence, length, structure, target-binding affinity, and/or the physicochemical properties of the target analyte. The subject invention provides methods, assays, and materials for rapid and specific detection of target molecules in a sample, in particular, in both clinical and field settings.

Advantageously, the methods and assays of the subject invention are simple to perform, sensitive, and have rapid turnaround times (on the order of seconds). The methods and assays provided by the subject invention also streamline the development and broaden the application of label-free and sensitive aptamer-based colorimetric on-site assays for the detection of multiple target analytes.

In one embodiment, the subject invention provides a method for detecting a target in a sample, the method comprising mixing/contacting non-covalent assemblies of an aptamer-dye complex with the sample. In the presence of the target, aptamer-target binding liberates the non-covalently bound nucleic-acid-binding dye complexed with the aptamer, resulting in optical changes that can be observed spectrophotometrically or with the naked eye.

In a specific embodiment, the dye is 3,3'-diethylthiatricarbocyanine (Cy7). In a preferred embodiment, the dye is 3,3'-di(3-sulfopropyl)-4,5,4',5'-dibenzo-9-methyl-thiacarbocyanine (MTC).

In one embodiment, the detection limits are at least the same or lower than the dissociation constant of the aptamer and target.

In one embodiment, the detection of the target comprises measuring a signal generated upon assembly of the aptamer-target complex. In another embodiment, the method further comprises determining the concentration of the target in the sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D show a schematic of aptamer-based dye-displacement assays. (A) DNA aptamers of varying length/sequence/structure can (B) bind to certain cyanine dyes in monomeric and/or dimeric form depending on the aptamer. Aptamer-dye binding increases the absorbance of these species and attenuates the formation of high order aggregates. (C) When the target is added to the aptamer-dye complex, the dye is displaced from the aptamer, which liberates the dye in solution and cause it to (D) conglomerate as high order aggregates, inducing a ratiometric change between monomer/dimer and aggregate absorbance in a target-concentration-dependent manner.

FIGS. 2A-2C show the development strategy for aptamer-based dye-displacement assays. (A) A hypothetical plot depicting the absorbance of monomeric/dimeric and aggregate forms of the dye as a function of aptamer concentration. As aptamer concentration is increased, dye monomer/dimer absorbance increases and aggregate absorbance decreases, and vice-versa. The sensitivity of the dye-displacement assay will vary based on the concentration of aptamer and dye employed, with maximum sensitivity being achieved in the range (blue region, peak of blue dotted curve) where small changes in aptamer concentrations result in the greatest change of dye absorbance. (B) Plot of the absorbance of Cy7 monomer and H-aggregate plotted against concentration of SCA2.1. (C) Calibration curves for MDPV detection using 2.5 µM Cy7 and 2 µM SCA2.1 (black) or 4 µM SCA2.1 (red). Signal gains were normalized to enable direct comparison of sensitivity between the two assays. Insert depicts normalized signal gains obtained at low concentrations of target.

FIGS. 3A-3B show the relationship between concentration of Cy7 and absorbance of solution in aqueous buffer. (A) Absorbance spectra of various concentrations of Cy7 dissolved in 10 mM Tris buffer (pH 7.4) containing 20 mM NaCl, 0.5 mM $MgCl_2$, 0.01% SDS, and 1% DMSO. In the systems tested herein, Cy7 monomer peak absorbance is 770 f 10 nm, Cy7 dimer peak absorbance is 675 nm, and Cy7 H-aggregate peak absorbance is 600 nm. (B) Plot of Cy7 absorbance at 600 nm versus dye concentration.

FIG. 4 shows the absorbance spectra of 2.5 µM Cy7 in the presence of 0, 0.25, 0.5, 0.75, 1, 1.5, 2, 3, or 4 µM SCA2.1 as indicated by the black-to-red color gradient.

FIGS. 5A-5B show the absorbance spectra of solutions containing 2.5 µM Cy7 with (A) 2 µM SCA2.1 in the presence of 0, 0.078, 0.16, 0.31, 0.63, 1.25, 1.90, 2.5, 3.8, 5.0, 6.3, 7.5, 10 µM MDPV or (B) 4 µM SCA2.1 in the presence of 0, 0.63, 1.25, 1.90, 2.5, 3.8, 5.0, 6.3, 7.5, 10, or 20 µM MDPV. Increasing MDPV concentration is indicated by the black-to-red color gradient.

FIG. 6 shows the photograph of MDPV detection with the Cy7-displacement assay taken after 5 min of mixing the aptamer-dye complex with target. [SCA2.1]=2.0 µM, [Cy7]=2.5 µM.

FIGS. 7A-7C show the detection of cocaine using 38-GC in the Cy7-displacement assay. (A) Absorbance spectra of solutions containing 2.5 µM Cy7 with various concentrations of 38-GC (black-to-red color gradient: 0, 1, 2, 3, 4, 5, 6, 7, 9, 11 µM) (left). Absorbance of Cy7 monomer at 765 nm and H-aggregate at 600 nm plotted against concentration of 38-GC (right). (B) Absorbance spectra of solutions containing 2.5 µM Cy7 and 4 µM 38-GC challenged with various concentrations of cocaine (black-to-red color gradient: 0, 0.5, 1, 2, 3.9, 7.8, 15.6, 31, 63, 125, 200, 250 µM) (left). The left panel depicts the corresponding calibration curve for cocaine detection; insert shows signal gain at low concentration (right). (C) Photograph of cocaine detection with the Cy7-displacement assay taken after 5 min of mixing the aptamer-dye complex with target.

FIG. 8 shows the spectra of 2.5 µM Cy7 in the presence of 0, 0.5, 1, 2, 3.9, 7.8, 15.6, 31, 63, 125, 200, or 250 µM cocaine. Black-to-red color gradient represents increasing concentrations of cocaine.

FIGS. 9A-9C show the detection of acetyl fentanyl using F14 in the Cy7-displacement assay. (A) Absorbance spectra of solutions containing 2.5 µM Cy7 with various concentrations of F14 (black-to-red color gradient: 0, 0.5, 1, 1.5, 2, 3 4, 5, 6, 7 µM) (left). Absorbance of Cy7 monomer at 770 nm, Cy7 dimer at 675 run, and H-aggregate at 600 nm plotted against concentration of F14 (right). (B) Absorbance spectra of solutions containing 2.5 µM Cy7 and 2 µM F14 challenged with various concentrations of acetyl fentanyl (black-to-red color gradient: 0, 0.08, 0.15, 0.31, 0.63, 1.25, 1.9, 2.5, 3.8, 5.0, 7.5, 10 µM) (left). The left panel depicts the corresponding calibration curve for acetyl fentanyl detection; insert shows signal gain at low concentrations of target (right). (C) Photograph of acetyl fentanyl detection with the Cy7-displacement assay taken after 5 min of mixing the aptamer-dye complex with target.

FIG. 10 shows the spectra of 2.5 µM Cy7 in the presence of 0, 0.08, 0.15, 0.31, 0.63, 1.25, 1.9, 2.5, 3.8, 5.0, 7.5, 10 µM acetyl fentanyl. Black-to-red color gradient represents increasing concentrations of acetyl fentanyl.

FIG. 11 shows the absorbance spectra of various concentrations of MTC (black-to-red color gradient 0, 0.5, 0.75, 1, 1.25, 1.5, 1.75, 2, 2.25, 2.5, 2.75, and 3 µM) dissolved in 10 mM Tris buffer (pH 7.4) containing 20 mM NaCl, 0.5 mM $MgCl_2$, 0.01% SDS, and 1% DMSO. In the systems tested herein, MTC monomer peak absorbance is 585 f 5 nm, MTC dimer peak absorbance is 545 nm, and MTC H-aggregate peak absorbance is 655 nm.

FIG. 12A-12D show the development of a colorimetric assay for MDPV detection based on SCA2.1 and MTC. (A) The absorbance of MTC at 655 nm plotted as a function of dye concentration. Chemical structure of the dye is shown. (B) Plot of the absorbance of MTC monomer and J-aggregate plotted against concentration of SCA2.1. (C) Calibration curves for MDPV detection using 2 µM MTC and 6 µM SCA2.1; insert depicts signal gains obtained at low concentrations of target. (D) Photographs of solutions with SCA2.1-MTC complex challenged with various concentration of MDPV taken after 5 minutes of target addition.

FIG. 18 shows the spectra of 1.6 µM MTC in the presence of 0, 1, 2, 4, 8, 16, 32, 64, 128, or 256 µM cocaine. Black-to-red color gradient represents increasing concentrations of cocaine. Insert shows absorbance of MTC at 655 nm plotted against concentration of cocaine present in the solution.

FIGS. 19A-19B show the absorbance of solutions containing MTC dissolved in 50% saliva. (A) Absorbance spectra of various concentrations of MTC (black-to-red color gradient 0, 0.5, 0.75, 1, 1.25, 1.5, 1.75, 2, 2.25, 2.5, 2.75, and 3 µM) dissolved in solutions containing 50% saliva and 10 mM Tris buffer (pH 7.4) containing 20 mM NaCl, 0.5 mM $MgCl_2$, 0.01% SDS, and 1% DMSO. (B) Plot of absorbance of MTC at 655 nm against concentration of MTC.

FIGS. 20A-20B show the binding of MTC to 38-GC in 50% saliva. (A) Absorbance spectra of solutions containing 1.6 µM MTC with various concentrations of 38-GC (black-to-red color gradient: 0, 2, 3, 4, 5, 6, 7, 8, 9 µM) in 50% saliva. (B) Absorbance of MTC monomer at 590 nm and J-aggregate at 655 nm plotted against concentration of 38-GC in both buffer and 50% saliva.

FIGS. 21A-21C show the detection of cocaine in 50% saliva using 38-GC and MTC. (A) Absorbance spectra of solutions containing 1.6 µM MTC and 6 µM 38-GC challenged with various concentrations of cocaine (black-to-red color gradient: 0, 1, 2, 4, 8, 16, 32, 64, 128, 256 µM) spiked in 50% saliva and (B) corresponding calibration curve for cocaine detection in both buffer and 50% saliva; insert shows signal gain at low concentrations of target. (C) Photograph of cocaine detection in 50% saliva with the MTC-displacement assay taken after 5 min of mixing the aptamer-dye complex with target.

FIGS. 22A-22C show the development of a colorimetric assay for acetyl fentanyl detection based on F14 and MTC. (A) Plot of the absorbance of MTC monomer and J-aggregate against concentration of F14 in both buffer (red) and 50% saliva (black). (B) Calibration curves for acetyl fentanyl detection using 2.5 µM MTC and 6 µM F14 in buffer (red) and 50% saliva (black); insert depicts signal gains obtained at low concentrations of target. (C) Photographs of solutions with F14-MTC complex challenged with various concentrations of acetyl fentanyl spiked in saliva taken after 5 minutes of target addition.

FIGS. 23A-23B show the binding of MTC to F14 in buffer and 50% saliva. Absorbance spectra of solutions containing 2.5 µM MTC with various concentrations of F14 (black-to-red color gradient: 0, 1, 2, 4, 5, 6, 7, 8, 9 µM) in (A) buffer and (B) 50% saliva.

FIGS. 24A-24B show the detection of acetyl fentanyl using F14 and MTC in buffer and 50% saliva. Absorbance spectra of solutions containing 2.5 µM MTC and 6 µM F14 challenged with various concentrations of acetyl fentanyl (black-to-red color gradient: 0, 0.05, 0.1, 0.2, 0.4, 0.8, 1.6, 3.2, 6.4, 12.8, 25.6, 51.2 µM) in (A) buffer and (B) 50% saliva.

FIGS. 29A-29B show the detection of THC using THC1.2 and MTC in buffer and 50% saliva. Absorbance spectra of solutions containing 2.5 µM MTC and 1.5 µM THC1.2 challenged with various concentrations of THC (black-to-red color gradient: 0, 0.038, 0.075, 0.15, 0.31, 0.63, 1.25, 2.5, 5, 10 µM) in (A) buffer and (B) 50% saliva.

FIG. 30 shows the spectra of 2.5 µM MTC in the presence of 0, 0.038, 0.075, 0.15, 0.31, 0.63, 1.25, 2.5, 5, 10 µM THC. Black-to-red color gradient represents increasing concentrations of THC. Insert shows absorbance of MTC at 655 nm plotted against concentration of THC present in the solution.

FIG. 31 shows the specificity of MTC-displacement assay based on the aptamer THC1.2. Absorbance spectra of solutions containing THC1.2-MTC complex challenged with THC, THC-COOH, and several different interferents including cannabidiol, cannabigerol, 4-fluoro MDMB-BUTINACA, MDMB-4-en-PINACA, heroin, methamphetamine, caffeine, nicotine, alprazolam, morphine, methadone, and fentanyl.

FIGS. 33A-33D show the detection of ochratoxin A using MTC and the aptamer OBA3. (A) Absorbance spectra of solutions containing 2.5 µM MTC with various concentrations of OBA3 (black-to-red color gradient: 0, 0.50, 0.75, 1, 1.25, 1.5, 2, 2.5 µM). (B) Absorbance spectra of solutions containing 2.5 µM MTC and 1.5 µM OBA3 challenged with various concentrations of THC (black-to-red color gradient: 0, 0.5, 1, 2, 3.9, 7.8, 15.5, 31, 62.5 µM). (C) Spectra of 2.5 µM MTC in the presence of 0, 0.5, 1, 2, 3.9, 7.8, 15.5, 31, 62.5 µM ochratoxin A. Black-to-red color gradient represents increasing concentrations of ochratoxin A. Insert shows absorbance of MTC at 655 nm plotted against concentration of ochratoxin A present in the solution. Experimental error is ~4%, but error bars are excluded due to narrow scaling of y-axis. (D) Photograph of ochratoxin A detection with the MTC-displacement assay taken after 5 min of mixing the aptamer-dye complex with target.

FIGS. 34A-34D show the detection of dopamine using MTC and a dopamine-binding aptamer. (A) Absorbance spectra of solutions containing 1.6 µM MTC with various concentrations of dopamine aptamer (black-to-red color gradient: 0, 4, 6, 8, 9, 10, 11, 12 µM). (B) Absorbance spectra of solutions containing 1.6 µM MTC and 8 µM dopamine aptamer challenged with various concentrations of dopamine (black-to-red color gradient: 0, 0.5, 1, 2, 4, 8, 16, 32, 64, 128 µM). (C) Spectra of 1.6 µM MTC in the presence of 0, 0.5, 1, 2, 4, 8, 16, 32, 64, 128 µM dopamine. Black-to-red color gradient represents increasing concentrations of dopamine. Insert shows absorbance of MTC at 655 nm plotted against concentration of dopamine present in the solution. Experimental error is ~2%, but error bars are excluded due to narrow scaling of y-axis. (D) Photograph of dopamine detection with the MTC-displacement assay taken after 5 min of mixing the aptamer-dye complex with target.

BRIEF DESCRIPTION OF SEQUENCES

Figure 13:
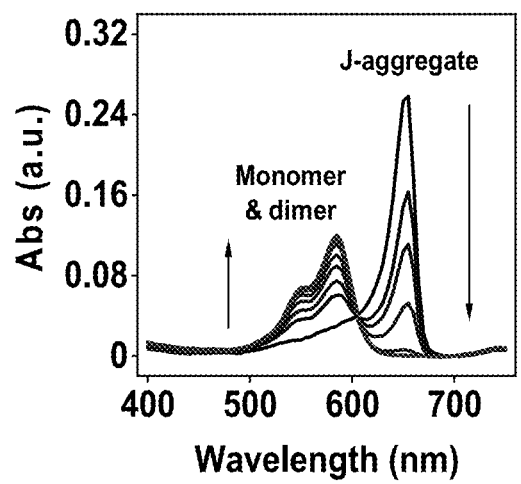
FIG. 13 shows the absorbance spectra of solutions containing 2 µM MTC with various concentrations of SCA2.1 (black-to-red color gradient: 0, 2, 3, 4, 5, 6, 7, 8, 9 µM).

SEQ ID NOs: 1-9 are sequences of DNA aptamers contemplated for use according to the subject invention.

DETAILED DESCRIPTION OF THE INVENTION

The subject invention provides methods, assays and materials for rapid and specific detection of a target analyte in a sample, in particular, in both clinical and field settings. In one embodiment, the method for detecting a target in a sample comprises mixing/contacting the sample with a non-covalent assembly of aptamer-dye complex, and detecting the target in the sample.

Advantageously, the methods and assays enable the utilization of aptamers in dye-displacement assay format with cyanine dyes regardless of aptamer sequence, length, structure, target-binding affinity, and the physicochemical properties of the target analyte. These assays can detect targets rapidly and with greater sensitivity and selectivity than conventional aptamer-based sensors.

Importantly, assay development does not require aptamer labeling or engineering. The methods of the subject invention can be paired with the existing aptamer isolation techniques, which can lead to the development of simple mix-and-measure assays that can be applied for various analytical applications. The aptamer-cyanine complexes can be generically applied for colorimetric small molecule detection in several contexts including medical diagnostics, forensics, food safety, and environmental monitoring.

In one embodiment, the detection of the target comprises measuring a signal generated upon the disassembly of the aptamer-dye complex and assembly of the aptamer-target complex. In another embodiment, the method further comprises determining the concentration of the target in the sample.

In one embodiment, the sample is a biological sample of a subject. In specific embodiments, the biological sample is selected from blood, plasma, urine, tears, sweat, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized sample, e.g., seized drug sample, for instance, a plant material sample, or a street drug sample seized by law enforcement or school or government officials.

Targets

The term "target" used herein extends to any molecule capable of being detected using an aptamer technique. In specific embodiments, the target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In another embodiment, the target may be an infective agent, antigen, toxin, disease biomarker and/or specific metal ion.

In one embodiment, the targets according to the subject invention are drug molecules, including cannabinoids such as natural cannabinoids, synthetic cannabinoids, cannabinoid derivatives and cannabimimetics. Cannabinoids include, but are not limited to, tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), arachidonoylethanolamine (Anandamide or AEA), 2-arachidonoylglycerol (2-AG), 2-arachidonyl glyceryl ether, N-arachidonoyl dopamine (NADA), virodhamine (OAE), lysophosphatidylinositol (LPI), naphthoylindoles, naphthylmethylindoles, naphthoylpyrroles, naphthylmethylindenes, phenylacetylindoles, adamantoylindoles, cyclohexylphenols, tetramethylcyclopropylindoles, indazole carboxamides, and quinolinyl ester.

In one embodiment, the target molecules according to the subject invention are selected from the fentanyl family, including fentanyl, its analogs, its derivatives and salts thereof. In a specific embodiments, the target molecules are fentanyl-related molecules that includes, but are not limited to, fentanyl, acetyl fentanyl, fentanyl, acrylfentanyl, butyryl fentanyl, valeryl fentanyl, cyclopropyl fentanyl, methoxyacetyl fentanyl, cis-3-methyl fentanyl, p-methoxy furanyl fentanyl, p-fluoro fentanyl, p-methoxy butyryl fentanyl, remifentanil, alpha-methyl thiofentanyl, o-methyl furanyl fentanyl, and p-fluoroisobutyryl fentanyl.

The "salts" can be with an inorganic acid, such as hydrochloric acid, hydrobromic acid, perchloric acid, nitric acid, thiocyanic acid, sulfuric acid, and phosphoric acid; an organic acid, such as citric acid, trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases.

In one embodiment, the target molecules are cathinones or synthetic cathinones, which include, but are not limited to, 3,4-methylenedioxypyrovalerone (MDPV); 4'-methyl-α-pyrrolidinohexanophenone (MPHP); naphyrone; methylone; ethylone; butylone; pentylone; mephedrone; mexedrone; buphedrone; pentedrone; hexedrone; heptedrone; α-pyrrolidinopropiophenone (α-PPP); 4'-methyl-α-pyrrolidinopropiophenone (M-α-PPP); 3',4'-methylenedioxy-α-pyrrolidinopropiophenone (MDPPP); 1-phenyl-2-(1-pyrrolidinyl)-1-pentanone (α-PVP); α-pyrrolidinohexiophenone (α-PHP); α-pyrrolidinoheptiophenone (α-PHpP, PV8); diethylpropion; pyrovalerone; dimethylcathinone; diethylcathinone; methcathinone; ethcathinone; 3-methylmethcathinone (3-MMC); 4-methylethcathinone (4-MEC); 3-chloromethcathinone (3-CMC); 4-chloromethcathinone (4-CMC); n-ethyl-nor-pentedrone (NEP); 3,4-methylenedioxy-α-pyrrolidinobutiophenone (MDPBP); 4-methyl-α-pyrrolidinobutiophenone (MEPBP); 4-fluoromethcathinone (4-FMC); n-ethyl-nor-hexedrone (Hexen); n-ethyl-nor-heptedrone; 4-ethylpentedrone; 4-methyl-NEP; and n-ethyl-nor-pentylone.

In specific embodiments, the target molecule is selected from cocaine, glucose, dopamine, serotonin, ochratoxin A, and mephedrone.

Aptamers

The aptamers of the subject invention are nucleic acid molecules characterized by the ability to bind to a target with high specificity and high affinity. The aptamer is an oligonucleotide, such as DNA or RNA molecules and may be single-stranded. In a preferred embodiment, the aptamer is a DNA aptamer.

As used herein, the terms "polynucleotide," "nucleotide," "oligonucleotide," and "nucleic acid" can be used to refer to a nucleic acid comprising DNA, RNA, derivatives thereof, or combinations thereof.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions such as hydrophobic and electrostatic interactions, hydrogen bonding, van der Waals forces, and n-n stacking as well as shape complementarity.

In certain embodiments, the aptamer according to the present invention may comprise at least 10, at least 20, at least 30, at least 40, at least 50, at least 60, at least 70, or at least 80 nucleotides. The aptamer, preferably, comprises 20 to 200 nucleotides, preferably 25 to 150 nucleotides, more preferably 30 to 100 nucleotides, most preferably, 35 to 60 nucleotides.

In one embodiment, the aptamer according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention may have free ends. For example, the 3' and 5' ends may not be ligated to form a loop, although they may be conjugated to other molecules or otherwise modified. The aptamers may adopt a tertiary structure such as a hairpin loop. In some embodiments, the aptamers may be looped. For example, the 5' and 3' ends of the nucleic acid are covalently bonded to form a loop not having any free ends.

In one embodiment, the aptamer according to the subject invention comprises at least one stem, two stems, or three stems. Each stem may be fully or partially complementary. Each stem may comprise the same or a different number of nucleotides. Exemplary lengths of each stem may be 1, 2, 3, 4, 5, 6, 7, 8, 9, 10, 11, 12, 13, 14, or 15 base pairs. Other exemplary lengths of each stem may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. A partially complementary stem may comprise more than one wobble base pair.

In one embodiment, the aptamer comprises at least one junction, which is formed when two or more stems meet. In certain embodiments, the junction may be a loop between two stems, or a three-way junction (TWJ). The junction may comprise, for example, 10, 11, 12, 13, 14, 15, 16, 17, 18, 19, 20, 21, 22, 23, 24, 25, 26, 27, 28, 29, or 30 nucleotides. The junction in an aptamer can serve as a binding domain for a target.

In one embodiment, the aptamer has at least one hairpin/stem-loop structure. The loop may have a minimum length of, for example, 10, 11, 12, 13, 14, 15, 16, 17, 18, 19, 20, 21, 22, 23, 24, 25, 26, 27, 28, 29, or 30 nucleotides. The loop may have a maximum length of, for example, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. The loop may comprise, for example, 20, 21, 22, 23, 24, 25, 26, 27, 28, 29, 30, 31, 32, 33, 34, 35, 36, 37, 38, 39, or 40 nucleotides.

In one embodiment, the aptamer comprises a nucleic acid sequence selected from SEQ ID Nos: 1-9 and sequences sharing at least 60%, 65%, 70%, 75%, 80%, 85%, 90%, 95%, 98%, 99% or 99.5% identity with a sequence selected from SEQ ID Nos: 1-9.

In one embodiment, the aptamer comprises two or more copies of the nucleic acid sequence selected from SEQ ID Nos: 1-9 and/or sequences sharing at least 60%, 65%, 70%, 75%, 80%, 85%, 90%, 95% or 99% identity with a sequence selected from SEQ ID Nos: 1-9.

In one embodiment, the aptamer is rich in G. For example, the aptamer comprises at least 10, 11, 12, 13, 14, 15, 16, 17, 18, 19, 20, 21, 22, 23, 24 or 25 Gs. The target-binding domain of the aptamer may comprise at least 5, 6, 7, 8, 9, 10, 11, 12, 13, 14, 15, 16, 17, 18, 19, or 20 Gs. In specific embodiments, the aptamer comprises 10, 11, 12, 13, 14, 15, 16, 17, 18, 19, 20, 21, 22, 23, 24 or 25 Gs. The target-binding domain of the aptamer comprises 5, 6, 7, 8, 9, 10, 11, 12, 13, 14, 15, 16, 17, 18, 19, or 20 Gs.

The aptamer of the present invention may or may not be truncated after isolation. The truncation may occur from 5',3' or both ends, up to 1, 2, 3, 4, 5, 6, 7, 8, 9, 10, 11, 12, 13, 14, 15, 16, 17, 18, 19 or 20 nucleotides.

The aptamers of the present invention may or may not include chemical modifications. The chemical modifications include a chemical substitution at a sugar position, a phosphate position, and/or a base position of the nucleic acid including, for example, incorporation of a modified nucleotide, incorporation of a capping moiety (e.g., 5' or 3' capping) or a tail moiety, conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-$NH_2$). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

In specific embodiments, the aptamer according to the subject invention may be modified by addition, subtraction, and substitution of one or more nucleotides from 5',3' or both ends or within sequences of the stem region of the aptamer. Advantageously, such addition, subtraction and substitution of one or more nucleotides from 5',3' or both ends of the aptamer may not affect the binding of the aptamer to small molecule targets. Such addition, subtraction and substitution of one or more nucleotides from 5',3' or both ends of the aptamer are well established in the art.

In one embodiment, the aptamer binds to the target with a dissociation constant of, for example, at least about 10 nM, about 50 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1 µM, about 2 µM, about 3 µM, about 4 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, or about 50 µM, or any value therebetween.

Method of Using the Aptamer

The subject invention provides methods and assays for rapid, sensitive and specific detection of a target in a sample. The aptamers according to the subject invention have high binding affinity and specificity for their targets, which enables their use for sensitive detection for analytical purposes.

In one embodiment, the subject invention provides an assay employing dye-displacement strategies for the detection of targets. In such assay, a small-molecule dye is initially associated with the binding domain of an aptamer. The presence of the target causes displacement of the dye from the binding domain, resulting in a change in the color, absorbance or fluorescence of the dye.

Advantageously, because the aptamers typically bind to these targets and dyes with similar affinities, the target-induced dye-displacement is more thermodynamically feasible than the displacement of a tightly-bound complementary strand. The aptamer used for such assay does not need to be labeled and can be label free. The dye-displacement assays can achieve a much lower detection limit.

In one embodiment, the method for detecting a target in a sample comprises mixing/contacting the sample with an aptamer-dye complex, and detecting the target in the sample, wherein the detection of the target comprises measuring an optical change generated upon the assembly of an aptamer-target complex and disassembly of the aptamer-dye complex, wherein the optical change can be detected spectrophotometrically or observed with the naked eye.

In one embodiment, the dye is a cyanine dye (e.g., MTC, Cy7, Cy7.5, Cy5, Cy5.5 and Cy3). Cyanine dyes have been widely employed as optical signal reporters in various biosensing platforms due to their ability to absorb and emit light over a wide range of wavelengths (300-1000 nm) with relatively high extinction coefficients. In general, these dyes can exist in different forms, including monomers, dimers, or higher-order aggregates, depending on the polarity of their immediate environment. Typically, cyanine dyes aggregate in aqueous solution due to their high hydrophobicity, but they can bind to DNA molecules like aptamers as monomers or dimers either within minor grooves or between nitrogenous bases. In preferred embodiments, the dye is Cy7 or MTC.

In one embodiment, the aptamer-dye complex comprises a dye binding to the target-binding domain, TWJ domain, hairpin structure, or bind within minor grooves, or between nitrogenous bases. Once the aptamer-dye complex dissembles in the presence of the target, the dye liberated by the target in the sample conglomerates as high order aggregates, resulting in a ratiometric change.

In one embodiment, the dye binds to the aptamer in a monomeric form in the absence of the target, reducing the formation of aggregates in a manner dependent on the concentration of the aptamer. In a specific embodiment, the dye binds to the aptamer in a form of both monomer and dimer.

In one embodiment, the assembly of aptamer-dye complex occurs in a aqueous solution comprising a ratio between the concentration of aptamer and dye. In specific embodiments, the ratio, i.e., [aptamer]:[dye], is, for example, 10:1, 9:1, 8:1, 7:1, 6:1, 5:1, 4:1, 3:1, 3:2, 2:1, 1:1, 1:2, 1:3, 2:3, 1:4, 1:5, 1:6, 1:7, 1:8, 1:9, 1:10 or any ratio therebetween.

In one embodiment, the dye may be used at for example, at least about 1 nM, about 5 nM, about 10 nM, about 50 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1 µM, about 2 µM, about 3 µM, about 4 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, or about 50 µM, or any value therebetween.

In one embodiment, the method further comprises determining the concentration of the target in the sample. The determination can comprise comparing the signal generated upon target binding with a standard curve of such signal. For example, the determination comprises comparing the absorbance signal generated upon binding of aptamer-target complex with a standard curve of the absorbance of the dye. The absorbance read-out can be quantified in seconds by, for example, a microplate-reader or portable photometer, allowing for high-throughput or on-site detection, respectively.

In certain embodiments, the aptamer comprises a nucleic acid sequence selected from SEQ ID NOs: 1-9 or a sequence sharing at least 60%, 65%, 70%, 75%, 80%, 85%, 90%, 95%, 98%, or 99% identity with a sequence selected from SEQ ID NOs: 1-9.

In certain embodiments, the colorimetric dye-displacement assay detects nanomolar concentrations of the target, even in, for example, urine and saliva in a label-free manner via instrumental means.

In some embodiments, the dye, e.g., Cy7 and MTC, may be used at a concentration ranging from about 0.01 µM to about 100 µM, from about 0.1 µM to about 90 µM, from about 0.1 µM to about 80 µM, from about 0.1 µM to about 70 µM, from about 1 µM to about 60 µM, from about 1 µM to about 50 µM, from about 1 µM to about 40 µM, from about 1 µM to about 30 µM, from about 1 µM to about 20 µM, or from about 1 µM to about 10 µM.

The method of the subject invention is remarkably simple, fast and specific. For example, the detection can be performed in a single reservoir, e.g., tube, containing the aptamer-dye complex and the sample of interest. In preferred embodiments, this colorimetric dye-displacement assay achieves instantaneous detection of as low as 50 nM target with the naked-eye.

Because the ratio of the color intensity of various forms of the dye is proportional to the concentration of the target, the method of the subject invention can be used to determine the concentration of the target in the sample.

In one embodiment, the subject invention further provides methods for detecting one or more targets in a sample. The method comprises contacting the sample with one or more aptamer-dye complexes, and detecting one or more targets in the sample, wherein the detection comprises measuring signals generated upon binding of one or more target to the binding domain of the aptamers.

Other forms of detection may also utilize the aptamers of the subject invention in, for example, electrochemical sensors, gold nanoparticle assays, enzyme linked aptamer sorbent assays (ELASA), pull down assays (immunoprecipitation), microplate/well assays, lateral flow assays and/or any other appropriate form of detection.

In some embodiments, the aptamer according to the subject invention may be used at a concentration from about 1 nM to about 10 mM, about 10 nM to about 5 mM, about 20 nM to about 2 mM, about 50 nM to about 1 mM, about 100 nM to about 500 µM, about 200 nM to about 200 µM, about 500 nM to about 100 µM, about 1 µM to about 50 µM, from about 1 µM to about 40 µM, from about 1 µM to about 30 µM, from about 1 µM to about 20 µM, from about 1 µM to about 10 µM, from about 2 µM to about 9 µM, from about 2 µM to about 8 µM, from about 2 µM to about 7 µM, from about 3 µM to about 6 µM, from about 4 µM to about 6 µM, and from about 5 µM to about 6 µM. In specific embodiments, the aptamer according to the subject invention may be used at a concentration of 1 nM, 10 nM, 20 nM, 25 nM, 50 nM, 100 nM, 200 nM, 500 nM, 1 µM, 2 µM, 3 µM, 4 µM, or 5 µM.

In one embodiment, the method according to the subject invention can achieve superior sensitivity for target detection at low micromolar or nanomolar concentration, for example, as low as about 200 µM, about 150 µM, about 100 µM, about 10 µM, about 1 µM, about 100 nM, about 10 nM, or about 1 nM.

In one embodiment, the methods for target detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, or about 50 minutes.

In another embodiment, the methods for target detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides a method for detecting target molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain.

In one embodiment, the subject invention also further provides a kit for detecting a target of interest, the kit comprising the aptamer-dye complex according to the subject invention and instructions for using such aptamer-based sensor to detect the target of interest.

The subject invention encompasses the use of sequences having a degree of sequence identity with the exemplified nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Experimental Section

Chemicals and Reagents.

Tris preset crystals (pH 7.4), sodium chloride, magnesium chloride, potassium chloride, sodium dodecyl sulfate, dimethyl sulfoxide (DMSO), acetaminophen, adenosine, caffeine, lactose, dopamine hydrochloride (HCl), serotonin HCl, cocaine HCl, and 3,3'-diethylthiatricarbocyanine (Cy7) iodide was purchased from Sigma Aldrich. Methanol was purchased from Fisher Scientific. Fentanyl HCl, acetyl fentanyl HCl, acryl fentanyl HCl, furanyl fentanyl HCl, p-methoxy acetyl fentanyl HCl, p-fluoro fentanyl HCl, heroin HCl, morphine sulfate hydrate, codeine phosphate hydrate, methamphetamine HCl, lorazepam, tetrahydrocannabinol (THC), cannabidiol, cannabigerol, 4-fluoro MDMB-BUTINACA, MDMB-4-en-PINACA, alprazolam, methadone HCl, 3,4,-methylenedioxypyrovalerone (MDPV) HCl, mephedrone HCl, and ochratoxin A were purchased from Cayman Chemicals. (−)-Nicotine was purchased from Cerilliant Corporation. Deionized water was acquired from a Millipore water system with resistivity of 18.2 MΩ×cm.

Oligonucleotides.

All DNA oligonucleotides were purchased from Integrated DNA Technologies (IDT, US). SCA2.1, 38-GC, and F14 were HPLC purified by IDT. All oligonucleotides were resuspended in molecular biology grade water and their concentrations were determined using a NanoDrop2000 spectrometer (Thermo Scientific). DNA sequences are listed below (written as 5'-3'):

```
SCA2.1:
                                        (SEQ ID NO: 1)
5' CTT ACG ACC TTA AGT GGG GTT CGG GTG GAG TTT
ATG GGG TCG TAA G 3'

38-GC:
                                        (SEQ ID NO: 2)
5' GGG TGA CAA GGA AAA TCC TTC AAT GAA GTG GGT
CAC CC 3'

F14:
                                        (SEQ ID NO: 3)
5' CTT ACG ACC GGT GTG CTC GGG GAA GGG GGC CCT
AGG TGG TCG TAA G 3'

THC1.2:
                                        (SEQ ID NO: 4)
5' CTT ACG ACC CAG GGG GGT GGA CAG GCG GGG GTT
AGG GGG GTC GTA AG 3'

OBA3:
                                        (SEQ ID NO: 5)
5' CGG GGC GAA GCG GGT CCC G 3'

Glucose Apt:
                                        (SEQ ID NO: 6)
5' ACG ACC GTG TGT GTT GCT CTG TAA CAG TGT CCA
TTG TCG T 3'

MMC1:
                                        (SEQ ID NO: 7)
5' CTT ACG ACC AGG GTT GGT TTC ATC GGT GGT GTA
ATA TGG TCG TAA G 3'

Dopamine Apt:
                                        (SEQ ID NO: 8)
5' CGA CGC CAG TTT GAA GGT TCG TTC GCA GGT GTG
GAG TGA CGT CG 3'

Serotonin Apt:
                                        (SEQ ID NO: 9)
5' CGA CTG GTA GGC AGA TAG GGG AAG CTG ATT CGA
TGC GTG GGT CG 3'
```

Optimizing Aptamer Concentration for Dye-Displacement Assay.

Buffer conditions and final concentrations of reagents are listed in Table 1.

TABLE 1

Conditions employed for aptamer-based dye-displacement assays.

| Aptamer | Dye | [Aptamer] tested | [Aptamer] for target detection | Buffer |
|---------|-----|------------------|-------------------------------|--------|
| SCA2.1 | 2.5 µM Cy7 | 0-4 µM | 2 µM | 10 mM Tris-HCl (pH 7.4), 20 |
| 38-GC | 2.5 µM Cy7 | 0-11 µM | 4 µM | nM NaCl, 0.5 mM MgCl$_2$, |
| F14 | 2.5 µM Cy7 | 0-7 µM | 2 µM | 0.01% (v/v) SDS, 1% (v/v) |
| SCA2.1 | 2.0 µM MTC | 0-9 µM | 5 µM | DMSO |

TABLE 1-continued

Conditions employed for aptamer-based dye-displacement assays.

| Aptamer | Dye | [Aptamer] tested | [Aptamer] for target detection | Buffer |
|---|---|---|---|---|
| 38-GC | 1.6 μM MTC | 0-9 μM | 5 μM (buffer) 6 μM (saliva) | |
| F14 | 2.5 μM MTC | 0-9 μM | 6 μM | |
| MMC1 | 1.8 μM MTC | 0-11 μM | 9 μM | |
| THC1.2 | 2.5 μM MTC | 0-2.5 μM | 1.5 μM | +2% (v/v) DMSO |
| OBA3 | 2.5 μM MTC | 0-2.5 μM | 1.6 μM | 10 mM Tris-HCl (pH 7.4), 20 mM NaCl 2 mM MgCl$_2$, 0.01% (v/v) SDS, 2% (v/v) DMSO |
| Dopamine Apt | 1.6 μM MTC | 0-12 μM | 8 μM | 10 mM Tris-HCl (pH 7.4), 20 mM NaCl, 4 mM KCl, 2 mM MgCl$_2$, 0.01% (v/v) SDS, 1% (v/v) DMSO |
| Glucose Apt | 1.8 μM MTC | 0-21 μM | 10 μM | |
| Serotonin Apt | 1.4 μM MTC | 0-14 μM | 8 μM | 10 mM Tris-HCl (pH 7.4), 140 mM NaCl, 4 mM KCl, 2 mM MgCl$_2$, 0.01% (v/v) SDS, 1% (v/v) DMSO |

TABLE 2

Dye-displacement assay performance for different aptamer-dye pairs.

| Aptamer/Dye | Time to observe color change | Observed color change | Spectra stabilization time |
|---|---|---|---|
| SCA2.1/Cy7 | <1 min | Clear to blue | 1 min |
| 38-GC/Cy7 | <1 min | Clear to blue | 1 min |
| F14/Cy7 | <1 min | Clear to blue | 1 min |
| SCA2.1/MTC | <1 min | Magenta to blue | 5 min |
| 38-GC/MTC | 2 min | Purple to blue | 5 min |
| F14/MTC | <1 min | Purple to blue | 5 min |
| THC1.2/MTC | 5 min | Magenta to blue | 5 min |
| OBA3/MTC | 1 min | Dark purple to dark blue | 1 min |
| MMC1/MTC | <1 min | Magenta to blue | 10 min |
| Dopamine Apt/MTC | <1 min | Purple to blue | 5 min |
| Serotonin Apt/MTC | 30 min | Blue to aquamarine | 60 min |
| Glucose Apt/MTC | N/A | N/A | 60 min |

TABLE 3

Characteristics of aptamers and targets used in this work.

| Aptamer | Length (nt) | Structure | Target/Charge at pH 7.4 |
|---|---|---|---|
| SCA2.1 | 46 | Parallel G-quadruplex | Synthetic cathinones (positively charged) |
| 38-GC | 38 | Three-way junction | Cocaine (positively charged) |
| F14 | 46 | Unknown | Acetyl fentanyl (positively charged) |
| THC1.2 | 47 | Parallel G-quadruplex | THC (hydrophobic, neutral) |
| OBA3 | 19 | Triple-stem with loop | Ochratoxin A (hydrophobic, negatively charged) |
| MMC1 | 46 | Unknown | Mephedrone (positively charged) |
| Dopamine Apt | 44 | Parallel G-quadruplex | Dopamine (positively charged) |
| Serotonin Apt | 44 | Anti-parallel G-quadruplex | Serotonin (positively charged) |
| Glucose Apt | 40 | Unknown | Glucose (neutral) |

To determine the optimal concentration of aptamer to employ with a given dye concentration, various concentrations of a particular aptamer dissolved in 200 μL of their respective reaction buffer was incubated for 10 min to permit aptamer folding. Then, 198 μL of this solution was added to PCR tubes containing 2 μL dye dissolved in 100% DMSO pipetted to the bottom of the tube. After light mixing, 75 μL of this mixture was added to the wells of a transparent 384-well microplate (Nunc) and absorbance spectra were recorded from 400 to 750 nm using a Tecan Infinite M1000 Pro (Switzerland) every 5 min for a total of 20 min. Background absorbance by the microplate itself was determined by scanning empty wells and subtracted prior to data analysis. Data was analyzed and plotted with Origin 9 Pro software. For experiments involving Cy7, absorbance peaks were observed for monomer at 760-775 nm, for dimer at 675 nm, and for H-aggregate at 6.00 nm. For experiments with MTC, absorbance peaks were observed for monomer at 585-590 nm (with a shoulder at 545 nm for dimer) and for J-aggregate at 650-655 nm.

Target Detection Using Dye-Displacement Assay.

Buffer conditions and final concentrations of reagents are listed in Table 1. To perform target detection using aptamer-dye complex, a particular concentration of aptamer was first dissolved in its respective buffer and incubated for 10 minutes to permit aptamer folding. Then, this aptamer solution was added to a PCR tube containing dye dissolved in 100% DMSO pipetted to the bottom to form aptamer-dye complexes. This solution was lightly mixed and 72 μL of this mixture was immediately added to tubes containing 8 ul target at various concentrations or interferent dissolved in buffer. Afterwards, 75 μL of the solution was added to the wells of a transparent 384-well microplate and absorbance spectra were recorded from 400 to 750 nm using a Tecan Infinite M1000 Pro every 5 minutes for a total of 15-90 min. Background absorbance from the microplate was subtracted prior to data analysis. Data was analyzed using Origin 9 Pro software. Signal gain was used as a metric of assay response and was determined using the following equation: $(R-R_0)/R_0$, where R and $R_0$ is equal to the ratio of peak aggregate absorbance to peak monomer absorbance (or monomer and dimer absorbance only in the case of F14 and Cy7) ($A_{aggregate}/A_{monomer}$) in the presence and absence of target/interferent, respectively. Photographs of the samples loaded in a 384-well white plate were taken using a Nikon D750 camera.

Experiments Performed in Saliva.

Pooled oral fluid collected from seven healthy drug-free consenting individuals (four male and three female) was first centrifuged at 20000 ref to remove semi-solid matter and then filtered using a 0.2 μm filter (Millipore). To evaluate DNA-dye binding in saliva, the protocol described above was used except that various concentrations of drug was spiked into 100% saliva. For performing the dye-displacement assay to detect targets, DNA-dye complex was prepared at 2-fold higher concentration in 2× reaction buffer, and 40 ul of this solution was mixed with 40 ul of saliva spiked with various concentrations of drug (at 2-fold higher concentration). The absorbance spectra of the solutions were determined as mentioned above.

Example 1—Study Rationale

Cyanine dyes have been widely employed as optical signal reporters in various biosensing platforms due to their ability to absorb and emit light over a wide range of wavelengths (300-1000 nm) with relatively high extinction coefficients. In general, these dyes can exist in different forms, including monomers, dimers, or higher-order aggregates, depending on the polarity of their immediate environment. Typically, cyanine dyes aggregate in aqueous solution due to their high hydrophobicity, but they can bind to DNA molecules like aptamers as monomers or dimers either within minor grooves or between nitrogenous bases.

The cyanine dye Cy7 has been used as a colorimetric signal reporter to detect cocaine with its corresponding DNA aptamer. The dye non-covalently binds within the three-way-junction structured binding domain of the aptamer as a monomer, and subsequent addition of the target causes the dye to be displaced into solution to form dimers, resulting in reduction of monomer absorbance.

In this system, an excess amount dye was used to ensure that the aptamer was saturated (dye:aptamer=2:1) to achieve high sensitivity, however the high level of background dimer led to no further changes occurring in dimer absorbance. Thus, the response of the assay to the target could only be assessed by changes in monomer absorbance. Theoretically, the responsiveness and sensitivity of this assay could be greatly enhanced if both monomer and aggregate absorbance changed upon the addition of target.

To this purpose, parameter(s) that significantly influenced dye-displacement assay functioning and performance were determined.

In the absence of target, the dye complexes with the aptamer, typically in a monomeric form, and reduces the formation of aggregates in a manner dependent on the concentration of the aptamer (FIGS. 1A-B). In the presence of target, target-induced dye displacement decreases monomer absorbance and concomitantly increases aggregate absorbance (FIGS. 1C-D).

Inferring from these results, assays employing high dye-aptamer ratios have high background signals, while, on the other hand, those that use high aptamer-dye ratios may be irresponsive to the target due to the high concentration of vacant aptamers and rebinding of dye monomers that are displaced by the target.

Therefore, given a particular concentration of dye, only a narrow range of aptamer concentrations could support sufficiently sensitive assay performance (FIG. 2A). Additionally, since every aptamer has a different sequence and secondary structure and thus varying affinity for a dye, the ratio of aptamer and dye must be empirically optimized to ensure sensitive assay performance.

Example 2—the Influence of Aptamer-Dye Ratio on Assay Response

As an initial model system, Cy7 and a 46-nt DNA aptamer termed SCA2.1 that binds to synthetic cathinone drugs such as methylenedioxypyrovalerone (MDPV) with nanomolar affinity ($K_D$ for MDPV 50 nM) were used. To select an appropriate dye concentration to employ, the absorbance properties of Cy7 in low ionic strength Tris buffer were first assessed. Increasing the concentration of dye in the range of 0-5 μM resulted in the formation of a proportionally increasingly broad absorption band spanning 540-900 nm with maxima at 600 nm corresponding to higher order H-aggregates, and a shoulder at 775 nm arising from Cy7 monomer (FIG. 3). H-aggregates consist of multiple Cy7 monomers stacked directly upon each other, and their absorbance spectra is blue-shifted relative to that of the monomer.

The capability of SCA2.1 to bind Cy7 as well as the extent of aptamer-dye complexation were then assessed by mixing various concentrations of SCA2.1 (0-4 μM) with a fixed concentration of 2.5 μM Cy7. In the presence of SCA2.1, a broad peak spanning from 540-695 nm with a maximum of 600 nm from H-aggregates and a sharp peak at 775 nm from dye monomer with an isosbestic point at 695 nm were observed. Increases in the concentration of SCA2.1 resulted in a large increase in monomer absorbance and relatively smaller decrease in H-aggregate absorbance, with saturation beginning to occur at 3 μM aptamer (FIG. 2B and FIG. 4). On the basis that near-zero aggregate background level was achieved at ~2 μM aptamer, and further increases in aptamer concentration resulted in only slight changes in monomer and aggregate absorption, performing target detection with more than 2 μM SCA2.1 would have reduced assay sensitivity.

To achieve high assay sensitivity, an aptamer concentration at which background was low and where the dye absorbance is most sensitive to changes in aptamer concentration was selected. This was confirmed by mixing different concentrations of the aptamer's target, methylenedioxypyrovalerone (MDPV) (0-20 μM), with solutions containing 2 μM SCA2.1 and 2.5 μM Cy7. The addition of target resulted in a decrease in absorbance at 775 nm and increase in absorbance at 600 nm, indicating the dye was being displaced by the target and then aggregating (FIG. 5A). The displacement and aggregation events were rapid, and the presence of target at low micromolar concentrations could be visually detected via a clear-to-blue color change with the naked eye (FIG. 6). The responsiveness of the assay (i.e. signal gain) was evaluated based on the difference of the ratio of monomer to aggregate peak absorbance in the presence versus the absence of target.

As seen in FIG. 2C, the assay was able to provide a linear response to MDPV over the range of 0-5 μM MDPV with an instrumental detection limit of 78 nM. The same assay was then performed with a greater aptamer-dye ratio (4 μM SCA2.1 and 2.5 uM Cy7). It had significantly poorer sensitivity compared to when 2 μM SCA2.1 was employed (FIG. 5B). This is evidenced by the greater steepness of the dose-response curve between 0 and 5 μM MDPV and the nearly 10-fold lower limit of detection (75 nM vs 600 nM) observed when 2 μM aptamer was used (FIG. 2C). This result clearly demonstrates that response and sensitivity of the dye displacement assay are profoundly affected by the ratio between the aptamer and dye.

Example 3—Generality of the Aptamer-Dye Ratio Parameter on Assay Performance

The various small-molecule binding DNA aptamers isolated to date have widely divergent sequences and structures such as hairpins, junctions, and G-quadruplexes. Therefore, to determine whether the ratio of aptamer and dye universally impacts dye displacement assay response and sensitivity, Cy7 with the three-way-junction structured 38-nt DNA aptamer 38-GC, which binds to cocaine with a $K_D$ of 2 µM, was tested.

First, varying concentrations of 38-GC (0-11 µM) was mixed with a fixed concentration of 2.5 µM Cy7 to determine the extent of aptamer-dye complexation. As with SCA2.1, increases in monomer absorbance (at ~765 nm) and decreases in H-aggregate absorbance occurred as the concentration of 38-GC was raised, with only slight changes in absorbance observed for either form of the dye above 6 µM aptamer (FIG. 7A). Therefore, for target detection, solutions containing 4 µM 38-GC and 2.5 µM Cy7 with cocaine in the range of 0-250 µM were challenged, obtaining a detection limit 4-fold lower than reported previously with the same assay by Stojanovic (0.5 µM vs 2 µM) and a visual detection limit of 8 µM (FIGS. 7B and 7C). As a control, it was determined that cocaine had no influence on Cy7 aggregation by mixing 2.5 µM Cy7 with various concentrations of cocaine. No perturbation of dye aggregation occurred in the presence of up to 250 µM cocaine (FIG. 8).

As a further demonstration of the generality of this assay development strategy, a dye-displacement sensor with a 46-nt G-rich DNA aptamer binding to acetyl fentanyl with nanomolar affinity termed F14 was created. The addition of F14 to 2.5 µM Cy7 resulted in spectral changes different from that observed with SCA2.1 and 38-GC: reduction of H-aggregate absorbance from 540-640 nm and increase in both H-dimer peak at 675 nm and monomer absorbance at 770 nm (FIG. 9A). Cyanine dimers can bind to DNA by binding within minor grooves. Since the absorption spectra of Cy7 did not change significantly beyond ~4 µM aptamer and the greatest changes in absorbance occurred between 1-2 µM aptamer, 2 µM F14 and 2.5 µM Cy7 were chosen for target detection in the range of 0-10 µM acetyl fentanyl. The addition of target resulted in concentration-dependent reductions in both monomer and dimer absorbance and increases in H-aggregate absorbance (FIG. 9B). In addition, the target could be visually detected via a faint green to dark blue color change (FIG. 9C).

Based on the ratiometric changes of the different forms of the dye, a calibration curve was constructed and it was determined that the assay had an instrumental detection limit of 80 nM with a linear range between 0-1.2 µM. As a control, it was determined that up to 10 µM acetyl fentanyl did not contribute to spectral changes in the H-aggregates (FIG. 10). The results taken together confirm that aptamer-dye ratio is a critical parameter that must be empirically optimized to guarantee sensitive assay response.

Example 4—Determining the Applicability of the Assay Development Strategy with Another Cyanine Dye To determine if the assay development principle could be extended to dyes other than Cy7, the cyanine dye 3,3'-di(3-sulfopropyl)-4,5,4',5'-dibenzo-9-methyl-thiacarbocyanine known as MTC was chosen.

The optical properties of MTC in aqueous buffer was first assessed by adding various concentrations of the dye (0-3 µM) to low ionic strength Tris buffer. A band from 500-690 nm was observed with a maxima at 655 nm, and the area and amplitude of the peak grew proportionally with the concentration of dye. These spectra indicated the presence of dye monomer and J-aggregates (FIGS. 11 and 12A). Then, the capability of MTC to bind SCA2.1 was tested by mixing 2 µM dye with various concentration of aptamer (0-9 µM). The addition of MTC to SCA2.1 resulted in concentration-dependent decreases in J-aggregate absorbance (655 nm) and an increase in a new peak at 585 nm with a shoulder at 550 nm, which corresponded to the formation of MTC monomer and dimer, respectively. Only slight changes in absorbance of either peak were observed beyond the addition of 6 µM SCA2.1 (FIG. 12B and FIG. 13). This result demonstrated that MTC could indeed bind to this aptamer in both monomer and dimer forms and the optimal concentration of aptamer to employ for target detection was ~6 µM.

Figure 14:
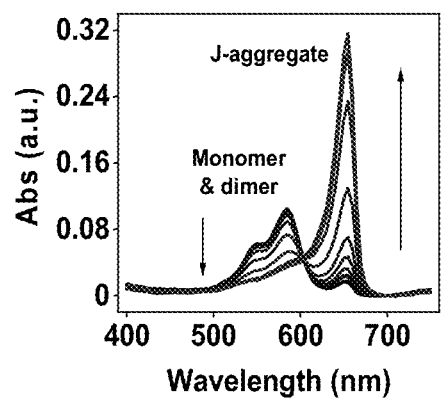
FIG. 14 shows the absorbance spectra of solutions containing 2 µM MTC and 5 µM SCA2.1 challenged with various concentration of MDPV (black-to-red color gradient: 0, 0.05, 0.1, 0.2, 0.4, 0.8, 1.6, 3.2, 6.4, 12.8, 25.6, 51.2 µM).

The ability of the target to displace bound MTC was assessed by mixing various concentrations of MDPV (0-51.2 µM) with solutions containing 6 µM SCA2.1 and 2 µM MTC. Clear target-concentration dependent decreases in monomer and dimer absorbance and increases in J-aggregate absorbance immediately occurred when MDPV was added to the aptamer-dye complex (FIG. 14). As expected, the assay was very sensitive and could detect as low as 50 nM MDPV via the use of a spectrometer (FIG. 12C) and 3.2 µM visually with the naked eye via a magenta-to-blue color change (FIG. 12D).

Figure 15:
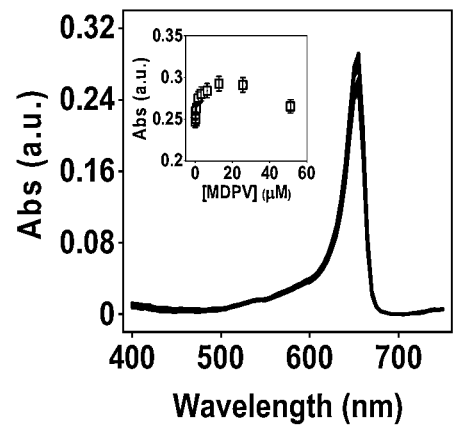
FIG. 15 shows the spectra of 2 µM MTC in the presence of 0, 0.05, 0.1, 0.2, 0.4, 0.8, 1.6, 3.2, 6.4, 12.8, 25.6, 51.2 µM MDPV. Black-to-red color gradient represents increasing concentrations of MDPV. Insert shows absorbance of MTC at 655 nm plotted against concentration of MDPV present in the solution.

Finally, whether MDPV itself could interact with the dye and perturb its aggregation was determined by mixing 2 µM MTC with various concentrations of MDPV. With the addition of 0.05-0.8 uM MDPV, J-aggregate absorbance at 655 nm did not vary significantly from solutions containing dye without target. At MDPV concentrations ≥1.6 µM, a slight and reproducible growth in peak absorbance was observed (~15%) (FIG. 15). This is not a concern however since the addition of ≥1.6 µM MDPV to SCA2.1-MTC complex resulted in increases in absorbance at 655 nm of at least 30-100-fold relative to blank. Therefore, it can be confirmed that signals produced in this assay are primarily and directly caused by target-induced displacement of dye and concomitant dye aggregation in aqueous buffer.

As another demonstration, whether MTC could be used with the cocaine-binding aptamer 38-GC for cocaine detection was determined. To do so, whether the aptamer could bind the dye was first determined by combining various concentrations of aptamer with a fixed concentration of 1.6 µM MTC. A lower concentration of dye was used with this aptamer as preliminary tests revealed that the aptamer binds weaker to the dye relative to SCA2.1.

Figures 16A, 16B:
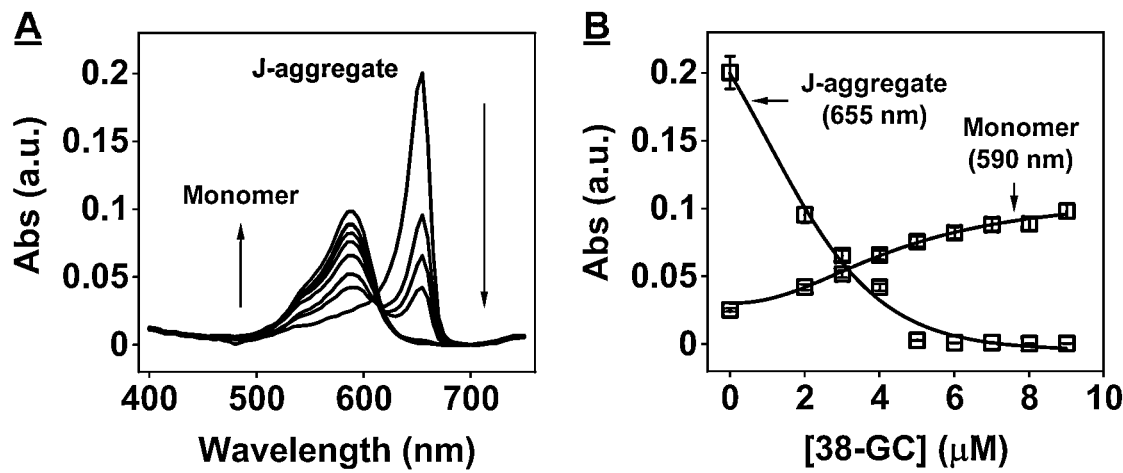
FIGS. 16A-16B show the binding of MTC to 38-GC. (A) Absorbance spectra of solutions containing 1.6 µM MTC with various concentrations of 38-GC (black-to-red color gradient: 0, 2, 3, 4, 5, 6, 7, 8, 9, µM). (B) Absorbance of MTC monomer at 590 nm and J-aggregate at 655 nm plotted against concentration of 38-GC.

As with SCA2.1, the addition of 38-GC to MTC resulted in the reduction of J-aggregate absorbance and an increase in monomer and dimer absorbance (FIG. 16A). No J-aggregate was detected above 5 µM aptamer, although the monomer peak continued to increase in amplitude even up to 9 µM aptamer (FIG. 16B).

Figures 17A, 17B:
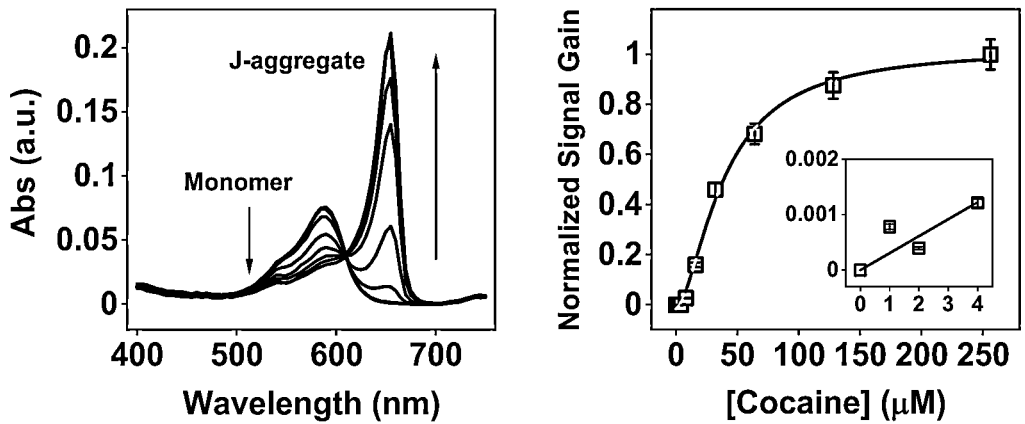
FIGS. 17A-17B show the detection of cocaine using MTC and 38-GC. (A) Absorbance spectra of solutions containing 1.6 µM MTC and 5 µM 38-GC challenged with various concentrations of cocaine (black-to-red color gradient: 0, 1, 2, 4, 8, 16, 32, 64, 128, 256 µM) and (B) corresponding calibration curve for cocaine detection; insert shows signal gain at low concentrations of target.

Based on these results, 6 µM 38-GC and 1.6 µM MTC were employed in the dye-displacement assay for cocaine detection to ensure both near-zero background without large sacrifices in assay sensitivity. The addition of cocaine to the aptamer-dye complex resulted in target-concentration dependent increases in J-aggregate absorbance and decrease in monomer and dimer absorbance within seconds, with an instrumental detection limit of 1 µM cocaine (FIG. 17).

Control experiments involving the addition of cocaine to the dye alone revealed that this target increases J-aggregate absorbance only slightly (14% at 256 µM cocaine relative to no cocaine). And again, the addition of target to the dye-aptamer complex induced several fold greater changes in J-aggregate absorbance compared to the addition of target to dye alone at every target concentration (FIG. 18O), meaning that signals were specifically being produced by target binding to the aptamer. The results therefore indicated that MTC is a good candidate for colorimetric aptamer-based small molecule detection.

Example 5—Generic Colorimetric Analyte Detection with MTC-Aptamer Complexes in Saliva To demonstrate the practical use of the dye-displacement assay for real-world applications, we determined if the dye-displacement assay could be applied to detect cocaine in saliva samples. First, the capability of MTC to aggregate in solutions containing 50% saliva (v/v) was assessed by adding dye in the range of 0-3 µM in solutions containing Tris buffer and saliva at a 1:1 ratio. The increase in J-aggregate absorbance over this concentration range was largely similar to that observed in pure buffer (FIG. 19).

To evaluate whether MTC could bind the aptamer in 50% saliva, various concentrations of 38-GC (0-9 µM) was mixed with 1.6 µM MTC. As with the results observed in buffer, increases in monomer and dimer absorbance and reduction in J-aggregate absorbance occurred with increasing concentrations of aptamer, although J-aggregate background levels were slightly higher in saliva (FIG. 20). This is perhaps because the ionic content and strength of saliva differs from our Tris buffer.

To perform target detection, solutions containing 6 µM 38-GC and 1.6 µM MTC with various concentration of cocaine (0-256 µM) spiked in 50% saliva were challenged. Similar target-concentration-dependent ratiometric changes occurred immediately upon the addition of cocaine, with an instrumental detection limit of 1 µM cocaine and visual detection limit of 16 µM cocaine in 50% saliva (FIG. 21). These results show the potential of MTC to be used in the dye-displacement assay to rapidly detect analytes in biological samples.

To further expand the generality of the dye-displacement assay and demonstrate its practical applicability, F14 with MTC to detect acetyl fentanyl in saliva were used. The addition of increasing concentrations of F14 in the range of 0-9 µM to 2.5 µM MTC resulted in an increase in monomer and dimer absorbance and decreases in J-aggregate absorbance both in buffer and 50% saliva (FIG. 22A and FIG. 23), demonstrating that the aptamer is capable of binding MTC and binding is not affected by saliva. The lowest level of J-aggregate absorbance was achieved at ~6 µM F14, and therefore this concentration was selected to perform target detection.

Figure 25:
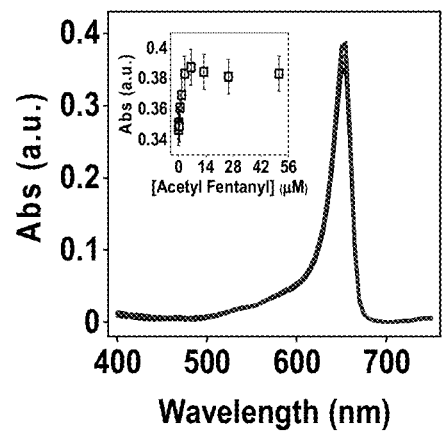
FIG. 25 shows the spectra of 2.5 µM MTC in the presence of 0, 0.05, 0.1, 0.2, 0.4, 0.8, 1.6, 3.2, 6.4, 12.8, 25.6, 51.2 µM acetyl fentanyl. Black-to-red color gradient represents increasing concentrations of acetyl fentanyl. Insert shows absorbance of MTC at 655 nm plotted against concentration of acetyl fentanyl present in the solution.

Upon the addition of acetyl fentanyl, target-concentration dependent ratiometric changes in monomer, dimer, and J-aggregate absorbance occurred in both buffer and 50% saliva, with linear ranges of 0-6.4 µM acetyl fentanyl and a detection limit of 50 nM in both matrices (FIG. 22B and FIG. 24). The assay is therefore sensitive enough to be applied for screening of acetyl fentanyl exposure in saliva, which has been reported to be present at low nanomolar levels. Visually, as low as 1.6 µM acetyl fentanyl can be detected in 50% saliva via a magenta-to-blue color change, suggesting that at least naked eye detection could be used to probe trace environmental acetyl fentanyl contamination (FIG. 22C). In the control test, acetyl fentanyl itself causes a small reproducible increase in MTC aggregation at target concentrations at or above 3.2 µM, but these increases are insignificant relative to those triggered by target-induced displacement of the dye from the dye-aptamer complex (FIG. 25).

Figure 26A:
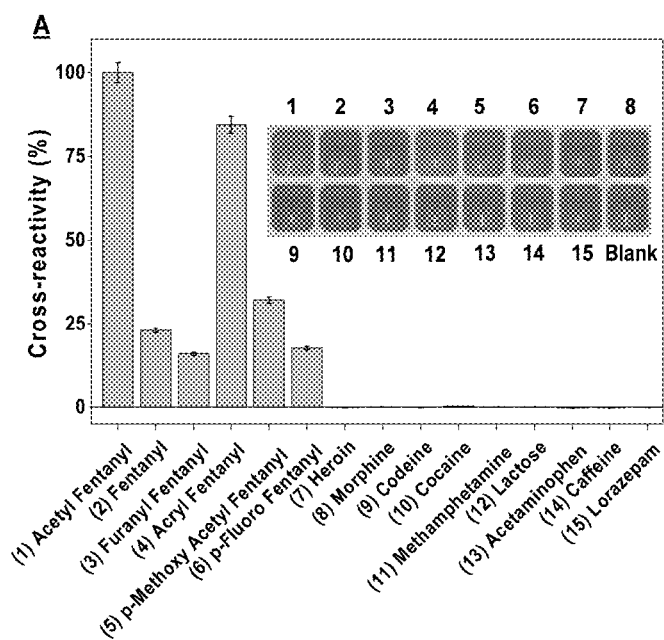
FIGS. 26A-26B show the specificity of MTC-displacement assay based on the aptamer F14. (A) Cross-reactivity of the assay to acetyl fentanyl and various analogs as well as interferents. Insert is a photograph of samples taken after 5 min of adding ligand to aptamer-dye complex. (B) Absorbance spectra of solutions containing F14-MTC complex challenged with various ligands.
Figure 26B:
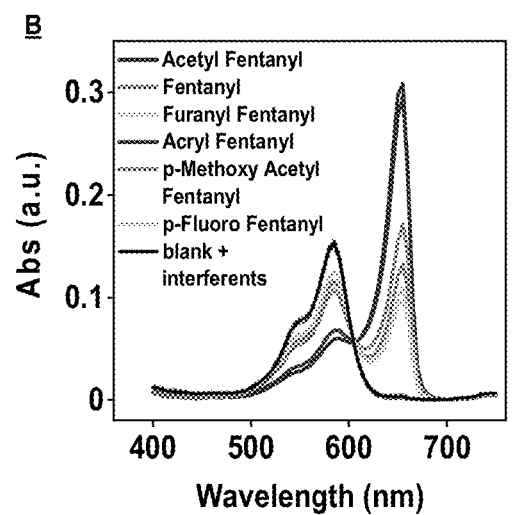

Finally, the specificity of this assay was demonstrated by challenging F14-MTC complexes with 10 µM of various analogs of acetyl fentanyl and 5-fold higher concentrations of interferents. The assay showed high cross-reactivity to acryl fentanyl with a visualizable magenta-to-blue color change and low to moderate cross-reactivity to fentanyl, furanyl fentanyl, p-methoxy acetyl fentanyl, and p-fluoro fentanyl with a magenta-to-purple color change (FIG. 26). Meanwhile, interferents such as the illicit drugs heroin, morphine, codeine, methamphetamine, cocaine, and lorazepam and the cutting agents caffeine, lactose, and acetaminophen, did not trigger any signal or color change, even at concentrations of 50 µM (FIG. 26). These results demonstrate that the dye-displacement assay is specific, and dye used in the assay is not subject to non-specific interactions with any tested compound, which have varied physicochemical properties.

As a final demonstration of the practical application of the assay, MTC and an isolated 47-nt G-rich DNA aptamer (termed THC1.2) were used to detect THC in saliva. Such an assay would be highly valuable for roadside identification of drivers that have recently used marijuana.

Figure 27A:
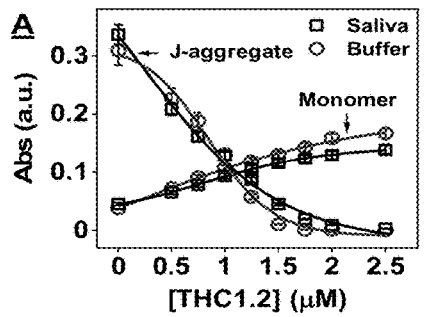
FIGS. 27A-27D show the development of a colorimetric assay for THC detection based on THC1.2 and MTC. (A) Plot of the absorbance of MTC monomer and J-aggregate plotted against concentration of THC1.2 in both buffer (red) and 50% saliva (black). (B) Calibration curves for THC detection using 2.5 µM MTC and 1.5 µM THC1.2 in buffer (red) and 50% saliva (black); insert depicts signal gains obtained at low concentrations of target. (C) Photographs of solutions with THC1.2-MTC complex challenged with various concentrations of THC spiked in saliva taken after 5 minutes of target addition. (D) Cross-reactivity of the assay to THC, urinary metabolite THC-COOH, and other interferents. Photographs of solutions containing THC1.2-MTC complex challenged with various ligands were taken after 5 minutes of ligand addition.
Figure 28A:
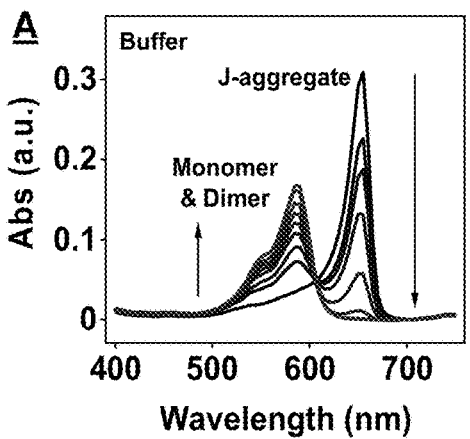
FIGS. 28A-28B show the binding of MTC to THC1.2 in buffer and 50% saliva. Absorbance spectra of solutions containing 2.5 µM MTC with various concentrations of THC1.2 (black-to-red color gradient: 0, 0.50, 0.75, 1, 1.25, 1.5, 2, 2.25, 2.5, 3.0 µM) in (A) buffer and (B) 50% saliva.
Figure 28B:
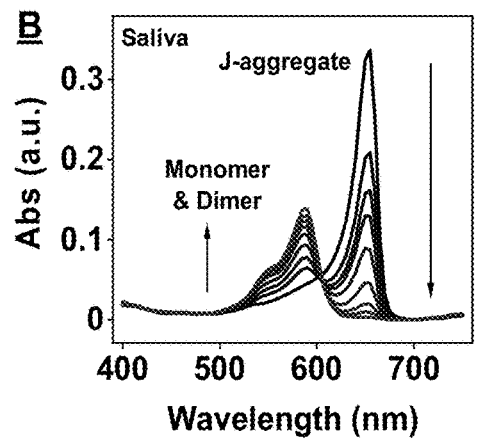
Figure 32A:
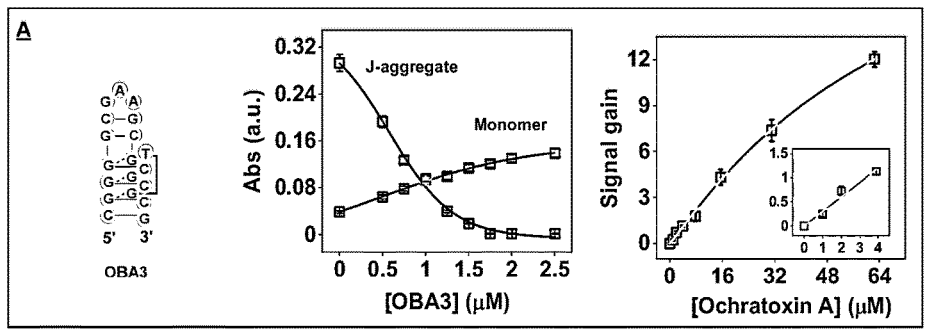
FIGS. 32A-32E show the generality of aptamer-based MTC-displacement assays for small-molecule detection. Secondary structure (left), aptamer-dye ratio optimization plot (middle), and target calibration curves (right) for (A) ochratoxin A-binding aptamer (SEQ ID NO: 5), (B) dopamine-binding aptamer (SEQ ID NO: 8), (C) serotonin-binding aptamer (SEQ ID NO: 9), (D) mephedrone-binding aptamer (MMC1) (SEQ ID NO: 7), and (E) glucose-binding aptamer (SEQ ID NO: 6).
Figure 32B:
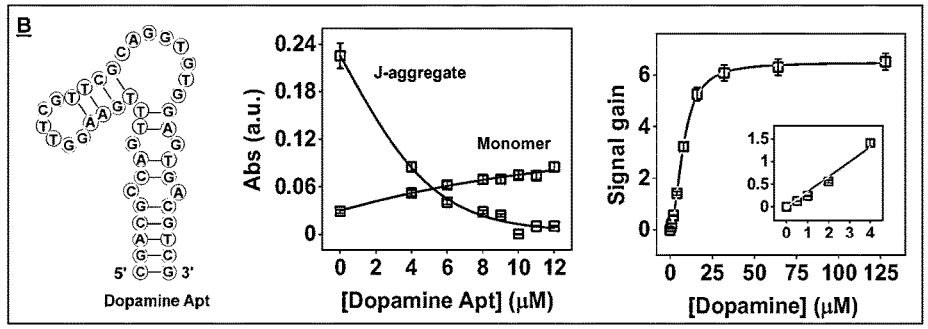
Figure 32C:
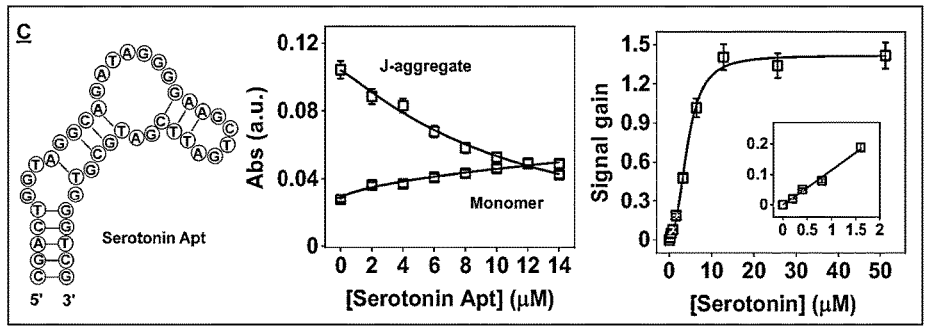
Figure 32D:
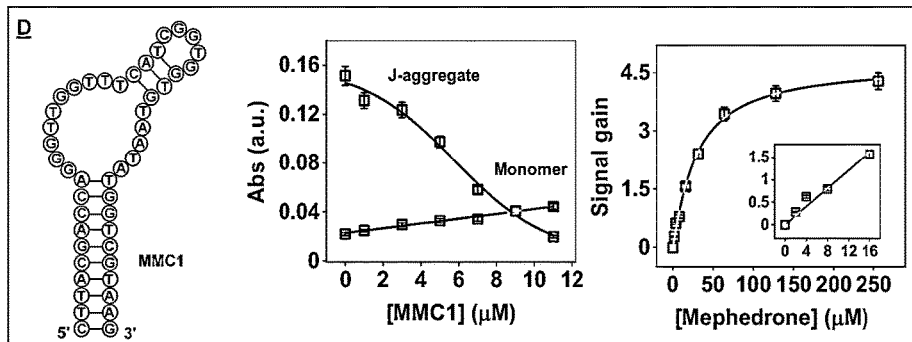
Figure 32E:
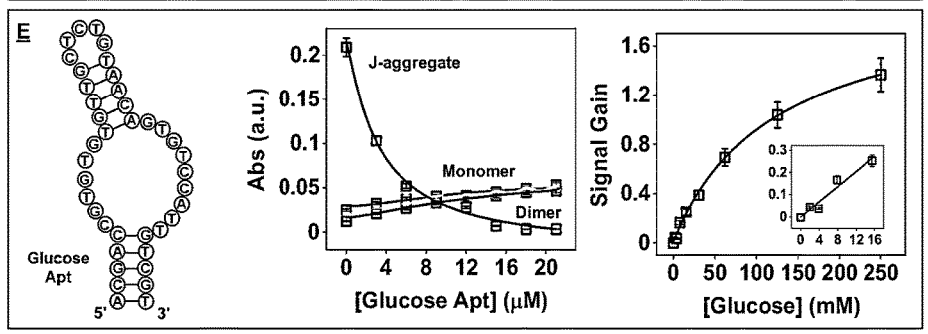
Figure 35A:
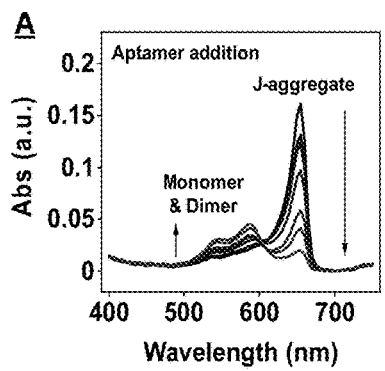
FIGS. 35A-35D show the detection of mephedrone using MTC and the aptamer MMC1. (A) Absorbance spectra of solutions containing 1.8 µM MTC with various concentrations of MMC1 (black-to-red color gradient: 0, 1, 3, 5, 7, 9, 11 µM). (B) Absorbance spectra of solutions containing 1.8 µM MTC and 9 µM MMC1 challenged with various concentrations of mephedrone (black-to-red color gradient: 0, 2, 4, 8, 16, 32, 64, 128, 256 µM). (C) Spectra of 1.8 µM MTC in the presence of 0, 2, 4, 8, 16, 32, 64, 128, 256 µM mephedrone. Black-to-red color gradient represents increasing concentrations of mephedrone. Insert shows absorbance of MTC at 655 nm plotted against concentration of mephedrone present in the solution. Experimental error is ~5%, but error bars are excluded due to narrow scaling of y-axis. (D) Photograph of mephedrone detection with the MTC-displacement assay taken after 5 min of mixing the aptamer-dye complex with target.
Figure 35B:
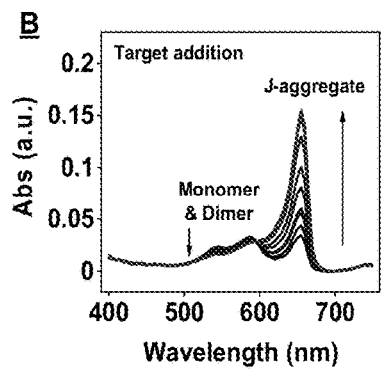
Figure 35C:
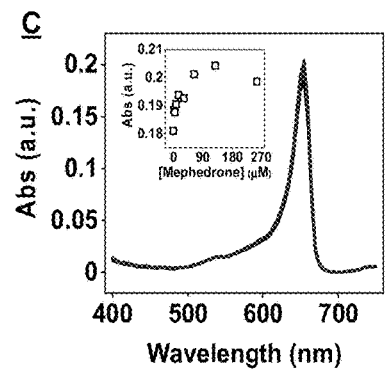
Figure 35D:
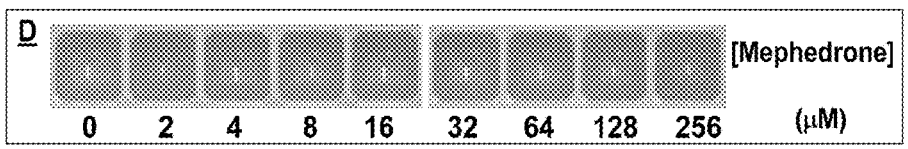
Figure 36A:
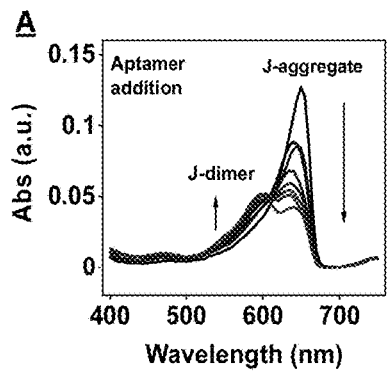
FIGS. 36A-36D show the detection of serotonin using MTC and a serotonin-binding aptamer. (A) Absorbance spectra of solutions containing 1.4 µM MTC with various concentrations of serotonin aptamer (black-to-red color gradient: 0, 2, 4, 6, 8, 10, 12, 14 µM). (B) Absorbance spectra of solutions containing 1.4 µM MTC and 8 µM serotonin aptamer challenged with various concentrations of serotonin (black-to-red color gradient: 0, 0.2, 0.4, 0.8, 1.6, 3.2, 6.4, 12.8, 25.6, 51.2 µM). (C) Spectra of 1.4 µM MTC in the presence of 0, 0.2, 0.4, 0.8, 1.6, 3.2, 6.4, 12.8, 25.6, 51.2 µM serotonin. Black-to-red color gradient represents increasing concentrations of serotonin. Insert shows absorbance of MTC at 655 nm plotted against concentration of serotonin present in the solution. Experimental error is ~2%, but error bars are excluded due to narrow scaling of y-axis. (D) Photograph of serotonin detection with the MTC-displacement assay taken after 60 min of mixing the aptamer-dye complex with target.
Figure 36B:
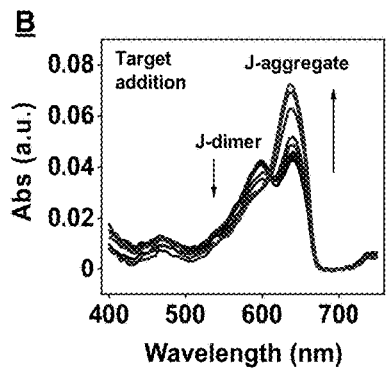
Figure 36C:
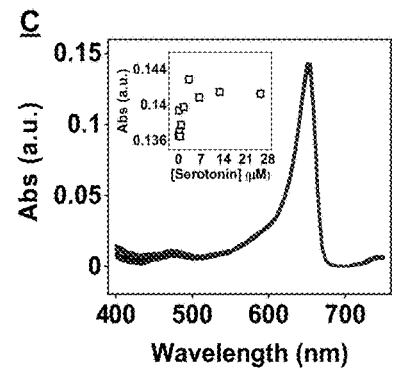
Figure 36D:
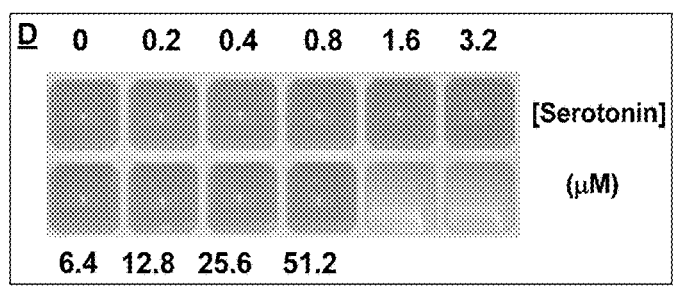

To assess aptamer-dye binding, a fixed concentration of 2.5 µM MTC was mixed with various concentrations of THC1.2 (0-2.5 µM) in buffer and 50% saliva. Regardless of the matrix, aptamer-concentration dependent increase in monomer and dimer absorbance and reduction in J-aggregate absorbance were observed, with no further changes occurring in absorbance at ~1.8 µM aptamer (FIG. 27A and FIG. 28). These results indicated that THC1.2 binds MTC with relatively high affinity compared to the previously tested aptamers.

Figure 27B:
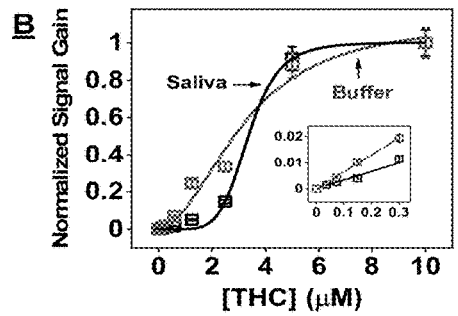
Figure 27C:
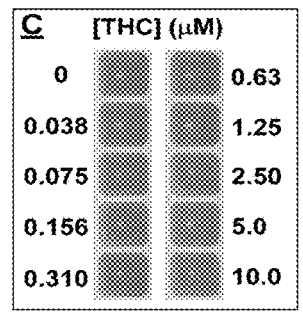

For target detection, various concentrations of THC (0-10 µM) were added to solutions containing 1.5 µM THC1.2 with 2.5 µM MTC in buffer or 50% saliva and observed ratiometric changes in dye absorbance (FIG. 27B and FIG. 29). However, assay response was far more sensitive in buffer relative to saliva, which is possibly due to non-specific association of THC with salivary proteins. Nevertheless, as low as 37.5 nM THC or 1.25 µM THC could be respectively detected in 50% saliva instrumentally with a linear range of 0-2.5 µM THC or visually via magenta-to-blue color change (FIG. 27C). No significant changes in J-aggregate absorbance were observed when MTC alone was mixed with up to 5 uM THC, although aggregate absorbance reduced slightly (10% relative to dye alone) and a shoulder peak was observed at 680 nm in the presence of 10 µM THC most likely due to the formation of THC-MTC aggregates (FIG. 30). This would not affect the practical application of the assay as the concentration of THC usually does not exceed 2 µM in human saliva.

Figure 27D:
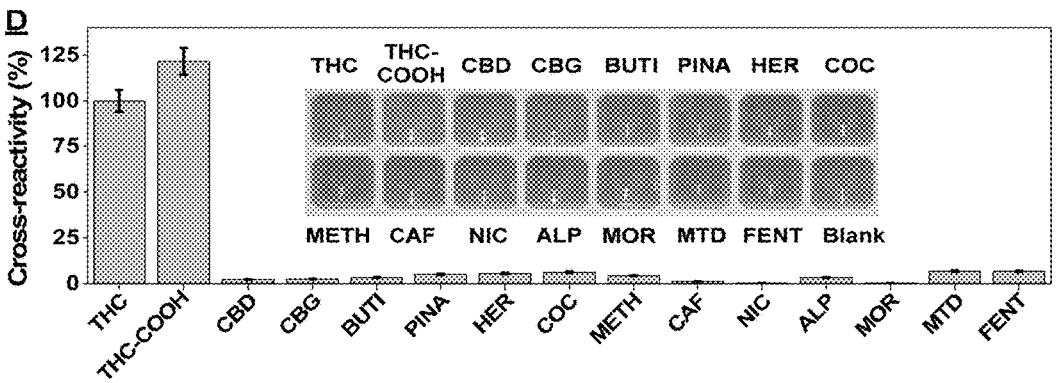

Assay specificity was determined by testing its response to 5 µM THC and structurally similar cannabinoids and interferents at 5-fold higher concentrations. Minimal cross-reactivity was observed to cannabidiol, cannabigerol, and other substances including 4-fluoro MDMB-BUTINACA (BUTI), MDMB-4-en-PINACA (PINA), heroin, methamphetamine, caffeine, nicotine, alprazolam, morphine, methadone, and fentanyl, except for a metabolite of THC, THC-COOH (FIG. 27D and FIG. 31). Coupled with the fact that the concentration of THC in saliva is ~1 µM up to an hour after marijuana consumption, these results indicate that the dye-displacement assay could be used to rapidly detect recent driver marijuana use in roadside settings.

Example 6—Establishing Generality of the MTC-Displacement Assay with DNA Aptamers of Various Sequence and Structure The binding and target-induced displacement of five more small-molecule-binding DNA aptamers with MTC were also evaluated. As seen in FIG. 32, these aptamers are diverse with regard to their size, sequence, and three-dimensional structure: an 19-nt ochratoxin A-binding aptamer containing a triple-stem structure (OTA3, $K_D$=1.4 µM), a stem-loop structured 46-nt aptamer that binds mephedrone with high specificity (MMC1, $K_D$=15 µM), and 44-nt dopamine-binding ($K_D$=150 nM) and 44-nt serotonin-binding aptamers ($K_D$=30 nM) with G-quadruplex features and a 40-nt glucose-binding aptamer ($K_D$=10 mM). All the aptamers could bind to MTC with varying levels of complexation, which was evaluated based on their capability to monomerize/dimerize MTC and reduce J-aggregate concentrations (FIG. 32). For instance, the addition of 1.5 µM OTA3 reduced J-aggregate absorbance to nearly zero, with dye monomerization seeming to cease at a 2.5 µM concentration of the aptamer. However, for the other aptamers, much greater concentrations of aptamer were required to reduce J-aggregate formation and maximize the aptamer-bound dye monomer and dimer. In particular, MMC1, dopamine aptamer, serotonin aptamer, and glucose aptamer required 10-20 µM to reach near-zero levels of J-aggregate absorbance (FIG. 33-36). This result highlight that different aptamers have divergent affinities for MTC, and emphasizes the necessity to optimize aptamer-dye ratios prior to evaluating whether a given aptamer-dye pair could enable target detection.

Nonetheless, selecting optimal aptamer-dye concentrations allowed to observe target-concentration-dependent reduction in monomer and dimer absorbance and increase in J-aggregate absorbance for all aptamers that could be measured instrumentally (FIGS. 33-36) and, for some cases, color changes could be identified with the naked eye.

Importantly, detection limits were similar to or below the reported dissociation constants of these aptamers. For example, it was possible to detect as low as 50 nM serotonin with its corresponding aptamer, which is expected given that the aptamer has a $K_D$ of 30 nM. On the other, it was only possible to detect low micromolar concentrations of ochratoxin (detection limit: 1 µM), mephedrone (detection limit: 2 µM), and millimolar glucose levels (detection limit: 2 mM) due to constrains imposed by the $K_D$s of their respective aptamers. It was also confirmed that the respective targets of the aptamers had minimal impacts on dye aggregation, in particular, only 1-5% increase in J-aggregate absorbance at the highest concentrations of tested analyte (FIG. 33-36). These results together demonstrate that the MTC can be generally applied with DNA aptamers regardless of their sequence, structure, target-binding affinity, or the physicochemical properties of the target for rapid and sensitive small molecule detection.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for detecting mephedrone in a sample, the method comprising
   a) mixing an aptamer with a dye to form an aptamer-dye complex, the aptamer comprising a nucleic acid sequence selected from SEQ ID NO: 7 and sequences sharing at least 95% sequence identity with SEQ ID NO: 7, and the dye being MTC;
   b) mixing/contacting the aptamer-dye complex with the sample; and
   c) detecting mephedrone in the sample by detecting an optical change generated upon the assembly of an aptamer-mephedrone complex and the disassembly of the aptamer-dye complex.

2. The method of claim 1, wherein the optical change can be observed with the naked eye or detected by a spectrometer.

3. The method of claim 1, wherein the dye non-covalently binds to the aptamer as a monomer or dimer.

4. The method of claim 1, the sample being a biological sample or an environmental sample.

5. The method of claim 4, the biological sample being selected from blood, plasma, urine, tears, and saliva.

6. The method of claim 1, the aptamer being SEQ ID NO: 7.

7. The method of claim 1, comprising in step c) detecting a decrease of absorbance at 770±10 nm and an increase of absorbance at 600 nm, or a decrease of absorbance at 585-590 nm and an increase of absorbance at 650-655 nm.

8. The method of claim 1, wherein the optical change can be detected spectrophotometrically.

9. A method for detecting mephedrone in a sample, the method comprising
   mixing/contacting non-covalent assemblies of aptamer-dye complex with the sample, the dye being MTC, and the aptamer comprising a nucleic acid sequence selected from SEQ ID NO: 7 and sequences sharing at least 95% sequence identity with SEQ ID NO: 7;
   measuring absorbance at 585-590 nm and 650-655 nm; and
   detecting methedrone in the sample by detecting a change in absorbance measured at 585-590 nm and 650-655 nm.

10. The method of claim 9, the sample being a biological sample or an environmental sample.

11. The method of claim 10, the biological sample being selected from blood, plasma, urine, tears, and saliva.

12. The method of claim 9, wherein the change in absorbance further leads to a color change that can be observed with the naked eye.

13. The method of claim 9, further comprising, prior to mixing/contacting non-covalent assemblies of aptamer-dye complex with the sample, mixing the aptamer with MTC, and detecting an increase of absorbance at 585-590 nm and a decrease of absorbance at 650-655 nm.

14. The method of claim 9, the change in absorbance being a decrease of absorbance at 585-590 nm and an increase of absorbance at 650-655 nm.

15. A method for detecting a cannabinoid in a sample, the method comprising
   a) mixing an aptamer with a dye to form an aptamer-dye complex, the aptamer comprising a nucleic acid sequence selected from SEQ ID NO: 4 and sequences sharing at least 95% sequence identity with SEQ ID NO: 4, and the dye being MTC;
   b) mixing/contacting the aptamer-dye complex with the sample; and
   c) detecting the cannabinoid in the sample by detecting an optical change generated upon the assembly of an aptamer-cannabinoid complex and the disassembly of the aptamer-dye complex.

16. The method of claim 15, wherein the optical change can be observed with the naked eye or detected by a spectrometer.

17. The method of claim 15, the sample being selected from blood, plasma, urine, tears, and saliva.

18. The method of claim 15, the biological sample being the aptamer being SEQ ID NO: 4.

19. The method of claim 15, the aptamer being used at a concentration of up to 2.5 μm.

20. The method of claim 15, the cannabinoid being selected from tetrahydrocannabinol (THC), tetrahydrocannabinolic acid (THCA), cannabinol (CBN), and tetrahydrocannabivarin (THCV).

* * * * *

SEQUENCE LISTING

```
<160> NUMBER OF SEQ ID NOS: 9

<210> SEQ ID NO 1
<211> LENGTH: 46
<212> TYPE: DNA
<213> ORGANISM: Artificial sequence
<220> FEATURE:
<223> OTHER INFORMATION: aptamer

<400> SEQUENCE: 1
cttacgacct taagtggggt tcgggtggag tttatggggt cgtaag          46

<210> SEQ ID NO 2
<211> LENGTH: 38
<212> TYPE: DNA
<213> ORGANISM: Artificial sequence
<220> FEATURE:
<223> OTHER INFORMATION: aptamer

<400> SEQUENCE: 2
gggtgacaag gaaaatcctt caatgaagtg ggtcaccc                   38

<210> SEQ ID NO 3
<211> LENGTH: 46
<212> TYPE: DNA
<213> ORGANISM: Artificial sequence
<220> FEATURE:
<223> OTHER INFORMATION: aptamer

<400> SEQUENCE: 3
cttacgaccg gtgtgctcgg ggaaggggggc cctaggtggt cgtaag          46

<210> SEQ ID NO 4
<211> LENGTH: 47
```

```
<212> TYPE: DNA
<213> ORGANISM: Artificial sequence
<220> FEATURE:
<223> OTHER INFORMATION: aptamer

<400> SEQUENCE: 4
cttacgaccc aggggggtgg acaggcgggg gttaggggggg tcgtaag                    47

<210> SEQ ID NO 5
<211> LENGTH: 19
<212> TYPE: DNA
<213> ORGANISM: Artificial sequence
<220> FEATURE:
<223> OTHER INFORMATION: aptamer

<400> SEQUENCE: 5
cggggcgaag cgggtcccg                                                    19

<210> SEQ ID NO 6
<211> LENGTH: 40
<212> TYPE: DNA
<213> ORGANISM: Artificial sequence
<220> FEATURE:
<223> OTHER INFORMATION: aptamer

<400> SEQUENCE: 6
acgaccgtgt gtgttgctct gtaacagtgt ccattgtcgt                             40

<210> SEQ ID NO 7
<211> LENGTH: 46
<212> TYPE: DNA
<213> ORGANISM: Artificial sequence
<220> FEATURE:
<223> OTHER INFORMATION: aptamer

<400> SEQUENCE: 7
cttacgacca gggttggttt catcggtggt gtaatatggt cgtaag                      46

<210> SEQ ID NO 8
<211> LENGTH: 44
<212> TYPE: DNA
<213> ORGANISM: Artificial sequence
<220> FEATURE:
<223> OTHER INFORMATION: aptamer

<400> SEQUENCE: 8
cgacgccagt ttgaaggttc gttcgcaggt gtggagtgac gtcg                        44

<210> SEQ ID NO 9
<211> LENGTH: 44
<212> TYPE: DNA
<213> ORGANISM: Artificial sequence
<220> FEATURE:
<223> OTHER INFORMATION: aptamer

<400> SEQUENCE: 9
cgactggtag gcagataggg gaagctgatt cgatgcgtgg gtcg                        44
```